(12) United States Patent
Jones et al.

(10) Patent No.: US 9,052,299 B2
(45) Date of Patent: Jun. 9, 2015

(54) VIAL CAPPER/DECAPPER FOR USE WITH A LIQUID TRANSFER SYSTEM

(75) Inventors: Lloyd A. Jones, Lenoir City, TN (US); Timothy R. Blevins, Englewood, OH (US); Robert A. Gabel, Troy, OH (US); Thomas Hoffmann, Beavercreek, OH (US)

(73) Assignee: Capitol Vial, Inc., Auburn, AL (US)

( * ) Notice: Subject to any disclaimer, the term of this patent is extended or adjusted under 35 U.S.C. 154(b) by 768 days.

(21) Appl. No.: 13/358,058

(22) Filed: Jan. 25, 2012

(65) Prior Publication Data

US 2012/0186200 A1 Jul. 26, 2012

Related U.S. Application Data

(60) Provisional application No. 61/435,898, filed on Jan. 25, 2011.

(51) Int. Cl.
*B67B 7/16* (2006.01)
*G01N 35/04* (2006.01)
*B65B 7/26* (2006.01)

(52) U.S. Cl.
CPC . *G01N 35/04* (2013.01); *B65B 7/26* (2013.01); *G01N 2035/0405* (2013.01); *G01N 2035/0413* (2013.01)

(58) Field of Classification Search
CPC ............ B67B 7/16; B67B 7/164; B67B 7/182
USPC ........ 53/381.4, 468; 81/3.33, 3.36, 3.39, 3.29
See application file for complete search history.

(56) References Cited

U.S. PATENT DOCUMENTS

| | | | | |
|---|---|---|---|---|
| 3,757,487 A | * | 9/1973 | Fauth | 53/334 |
| 3,775,829 A | * | 12/1973 | Rice | 29/426.3 |
| 3,987,535 A | * | 10/1976 | Brown | 29/426.4 |
| 4,442,735 A | * | 4/1984 | Chance et al. | 81/3.44 |
| 4,773,285 A | * | 9/1988 | Dionne | 81/3.2 |
| 4,807,425 A | | 2/1989 | Abrams | |
| 5,133,470 A | | 7/1992 | Abrams et al. | |
| 5,481,946 A | * | 1/1996 | Nishikawa et al. | 81/3.2 |
| 6,115,992 A | * | 9/2000 | Bankuty et al. | 53/308 |

(Continued)

OTHER PUBLICATIONS

Merit Automation LLC, Brochure, http://meritautomation.com/main_frame.html, Nov. 30, 2010 (1 page).

(Continued)

*Primary Examiner* — Gloria R Weeks
(74) *Attorney, Agent, or Firm* — Wood, Herron & Evans, LLP

(57) ABSTRACT

A liquid transfer system is disclosed including a transport path that transports a plurality of vials through the liquid transfer system. Each of the plurality of vials has a cap that forms a seal with an open-ended vial body. The liquid transfer system is comprised of a vial capper/decapper assembly that is positioned adjacent to the transport path and includes a plurality of rotatable spindles. Each spindle has a rotatable shaft and a first projection supported by the shaft. The first projection also includes a cam surface that engages a cap of a vial so as to breach the seal and open the vial. The plurality of spindles is rotated simultaneously to simultaneously breach the seals and open the caps of the plurality of vials.

40 Claims, 20 Drawing Sheets

(56) References Cited

U.S. PATENT DOCUMENTS

| | | | |
|---|---|---|---|
| 6,367,301 B1 * | 4/2002 | Bassani | 72/94 |
| 6,531,096 B1 | 3/2003 | Deveney et al. | |
| 7,159,489 B2 * | 1/2007 | Itoh | 81/3.2 |
| 7,207,241 B2 * | 4/2007 | Itoh | 81/3.2 |
| 8,297,151 B1 * | 10/2012 | Huppenthal et al. | 81/3.2 |
| 8,703,056 B2 * | 4/2014 | Sakairi et al. | 422/67 |
| 2009/0255376 A1 * | 10/2009 | Taylor | 81/3.2 |
| 2010/0116876 A1 | 5/2010 | Miller et al. | |

OTHER PUBLICATIONS

Capitol Vial Inc., Plastic Solutions, http://capitolvial.com/tech/capitol_vial_sm.pdf, Technical Information, Product Brochure (2003), Mar. 5, 2012 (12 pages).

Tecan Group Ltd., Freedom EVO, Features, http://www.tecan.com/platform/apps/product/index.asp?MenuID=2779&ID=5410&Menu=1&Item=21.1.8.7, Nov. 28, 2010 (1 page).

KMC Systems, Laboratory Instrument Design and Manufacture, http://www.kmcsystems.com/experience/laboratory-automation.php, Nov. 22, 2010 (1 page).

* cited by examiner

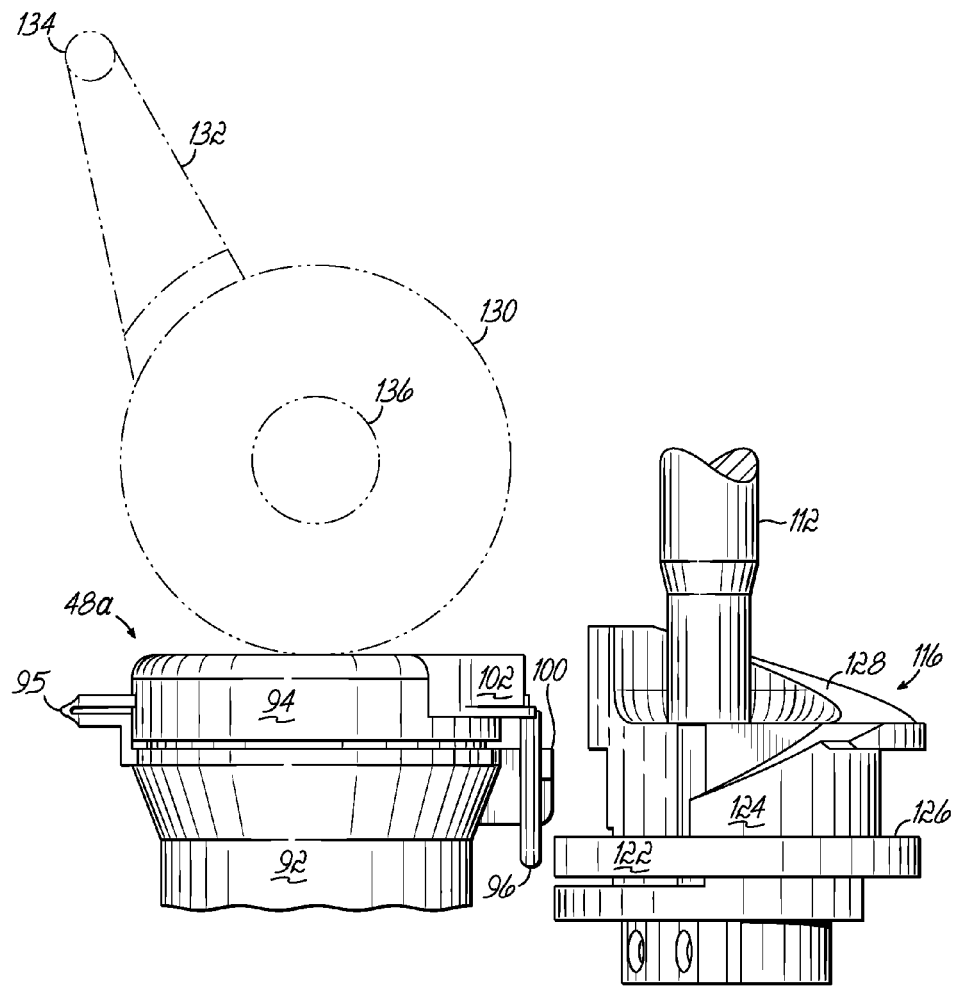
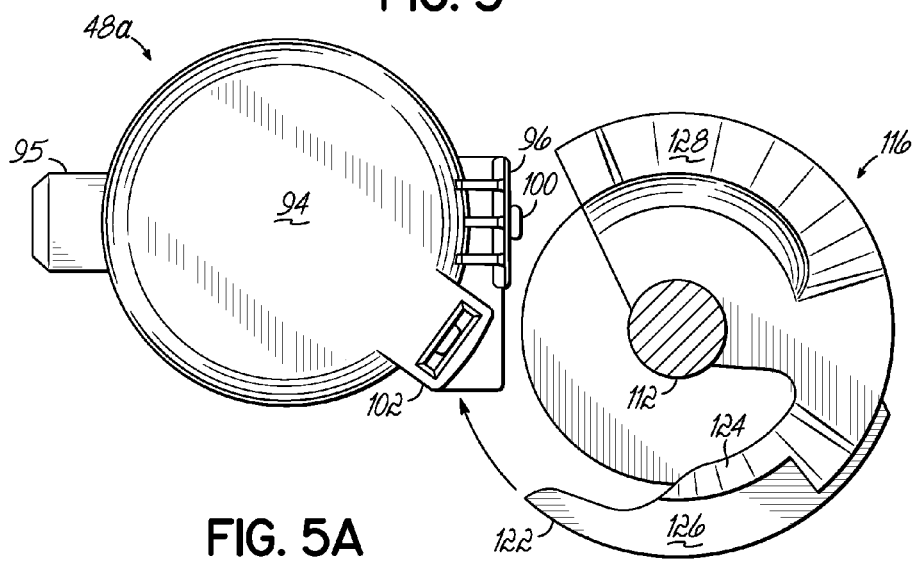

VIAL CAPPER/DECAPPER FOR USE WITH A LIQUID TRANSFER SYSTEM

The present application claims the filing benefit of U.S. Provisional Application Ser. No. 61/435,898, filed Jan. 25, 2011, the disclosure of which is incorporated herein by reference in its entirety.

FIELD OF THE INVENTION

The present invention relates generally to systems and methods for opening and closing the lid of a vial and, more particularly, to a system and method for automatic opening and closing the lid of a specimen vial.

BACKGROUND OF THE INVENTION

Biological fluid specimens are useful for diagnostic testing purposes and some biological fluid specimens, such as urine and saliva, are relatively easy to acquire as compared to blood or spinal fluid collection. Testing and analysis of urine and saliva are beneficial for determining, for example, kidney and bladder function, hormone levels, therapeutic drug levels, metabolisms, dehydration, and the detection of drugs-of-abuse.

Biological fluids for the prescribed analysis are often collected at the physician's office or at a clinic and then sent off site for the analysis. The patient is often times given a vial or container having a closure for collecting and sealing the biological fluid. Often the vial includes a safety, or tamper-proof, component particularly for use with the collection of a biological fluid for a drug-of-abuse analysis.

Typically, biological fluid specimens are collected in amounts that exceed those required for a particular analysis and only a sampling of the biological fluid specimen is necessary. Therefore, each vial containing a separate biological fluid specimen for analysis must be opened, or decapped, the sampling transferred to an analysis vessel, and the vial recapped for storage or disposal. Some automated systems have been developed for the decapping/recapping of the vials; however, there remains the need for a fully automated process that can decap multiple vials, transfer the sampling of biological fluid to multiple analysis vessels, and recap the vials in an efficient manner.

SUMMARY OF THE INVENTION

The present invention overcomes the foregoing and other shortcomings and drawbacks of known conventional vial cappers and decappers. While the invention will be described in connection with certain embodiments, it will be understood that the invention is not limited to these embodiments. On the contrary, the invention includes all alternatives, modifications, and equivalents as may be included within the spirit and scope of the present invention.

According to one illustrative embodiment of the invention, a liquid transfer system is described. The liquid transfer system includes a transport path that transports a plurality of vials through the liquid transfer system. Each of the plurality of vials has a cap that forms a seal with an open-ended vial body. The liquid transfer system is comprised of a vial capper/decapper assembly that is positioned adjacent to the transport path and includes a plurality of rotatable spindles. Each spindle has a rotatable shaft and a first projection supported by the shaft. The first projection also includes a cam surface that engages a cap of a vial so as to breach the seal and open the vial. The plurality of spindles is rotated simultaneously to simultaneously breach the seals and open the caps of the plurality of vials.

In another illustrative embodiment of the invention, a liquid sample transfer system is described. The liquid transfer system includes a transport path that transports at least one vial through the liquid transfer system. The vial has a cap that forms a seal with an open-ended vial body. The liquid transfer system is comprised of a vial capper/decapper assembly that includes at least one spindle. The spindle is positioned adjacent to the transport path and has a rotatable shaft and a first projection supported by the shaft. The first projection also includes a cam surface that engages a cap of a vial so as to breach the seal and open the vial. The capper/decapper assembly also includes a rotating arm assembly. The rotating arm assembly is positioned adjacent to the transport path and is opposite the at least one spindle. The rotating arm assembly engages the opened cap of the vial and retracts the cap away from the vial body.

In one embodiment, the rotating arm assembly includes an arm that extends radially therefrom. The arm is configured to engage the opened cap.

According to another illustrative embodiment, an automated liquid sample transfer system is described. The automated liquid transfer system includes a transport path that transports a plurality of vials, each containing a biological fluid, through the liquid transfer system. Each of the plurality of vials has a cap that forms a seal with an open-ended vial body. The automated liquid sample transfer system is comprised of a load module, an unload module, and a transfer module positioned between the unload and load modules. The transfer module further includes a vial capper/decapper assembly that is positioned adjacent to the transport path and includes a plurality of rotatable spindles. Each spindle has a rotatable shaft and a first projection supported by the shaft. The first projection also includes a cam surface that engages a cap of a vial so as to breach the seal and open the vial. The plurality of spindles is rotated simultaneously to simultaneously breach the seals and open the caps of the plurality of vials.

In still another illustrative embodiment of the invention, a method of capping/decapping a plurality of vials is described. Each of the vials has a cap that forms a seal with an open-ended vial body. The method includes aligning the plurality of vials with a plurality of rotatable spindles. Each spindle has a rotatable shaft and a first projection supported by the shaft. The first projection also includes a cam surface. The plurality of spindles is simultaneously rotated such that the first projection of each of spindle breaches the seal of each of the plurality of vials. With continued simultaneous rotation, the cam surface opens the caps of plurality of vials.

Yet another illustrative embodiment of the invention is directed to a method of transferring biological fluids from a first plurality of vials to a plurality of vessels. The method includes determining the number of unsampled vials within the first plurality of vials and the number of available vessels within the plurality of vessels. The number of biological fluids that are transferred is the lesser of the number of unsampled vials and the number of available vessels.

In accordance with yet another embodiment of the invention, a method of transferring biological fluids from a first plurality of vials to a plurality of vessels is described. A number of unsampled vials within the first plurality of vials is determined and compared with number of sampling channels. Then, if the number of unsampled vials is greater than the number of sampling channels, the number of biological fluids transferred is equal to the number of sampling channels; if the number of unsampled vials is less than the number of sampling channels, a second plurality of vials containing biological fluids is loaded and the number of biological fluids transferred is equal to the number of sampling channels; or if the number of unsampled vials is less than the number of sampling channels and there is no second plurality of vials available, the number of biological fluids transferred is equal to the number of unsampled vials.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIGS. 5-9 are side elevational views of an exemplary process of decapping a vial with the capper/decapper assembly of FIG. 3B.

FIGS. 5A-9A are top views of the process illustrated in FIGS. 5-9, respectively.

DETAILED DESCRIPTION OF THE INVENTION

Figure 1:
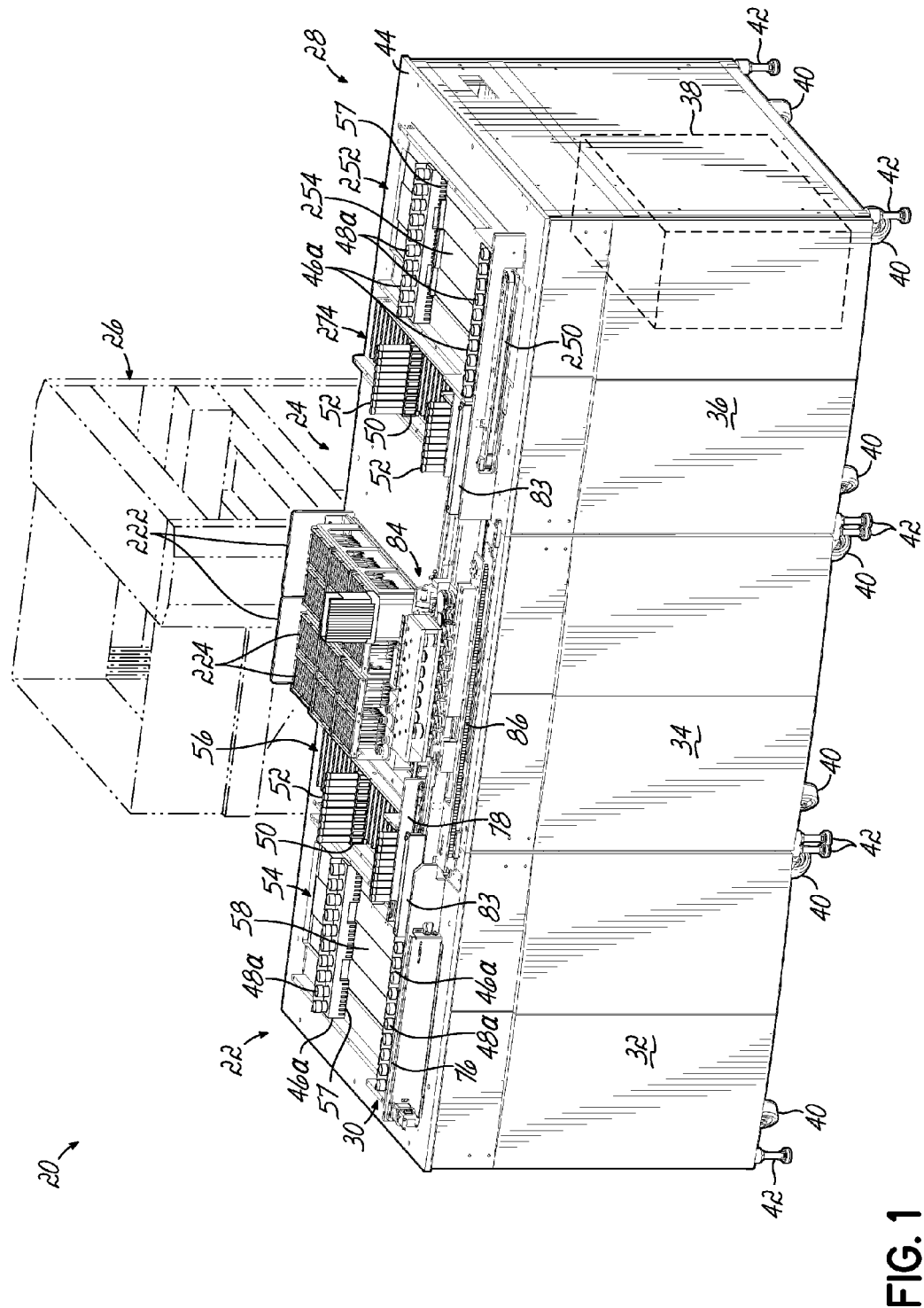
FIG. 1 is a perspective view of an automated vial capper/decapper station in accordance with one embodiment of the present invention.
Figure 2:
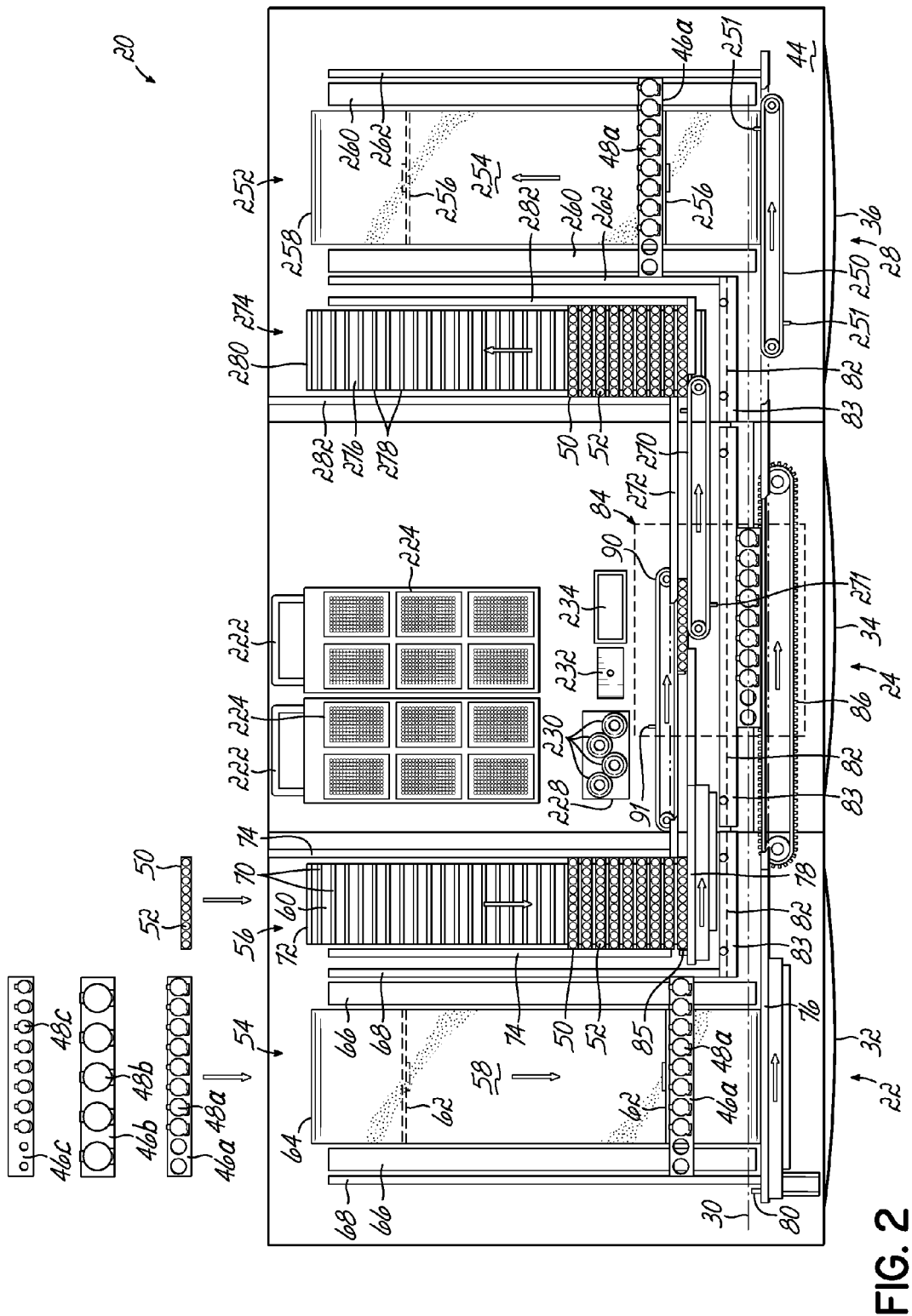
FIG. 2 is a top view of a unitary working surface of the automated vial capper/decapper station of FIG. 1.

Turning now to the figures, and more particularly to FIGS. 1 and 2, the details of an automated vial capper/decapper station ("automated station" 20) according to one embodiment of the present invention are illustrated. The automated station 20 includes a load module 22, a transfer module 24 having a fluid handling system 26 attached thereto, an unload module 28, and a transport path 30 extending between the three modules 22, 24, 28.

The fluid handling system 26 may generally include a pipetter (not shown) know to those of ordinary skill in the art and having any number of fluid channels, such as a single channel, a linear array of 8-, 12-, or more channels, or a plurality of channels organized into a matrix. The suitable fluid handling system 26 may include, for example, an original equipment manufacture ("OEM") pipetter that may be adapted to the particular transfer module 24. The fluid handling system 26 may include one or more robotics, operable by a computing system and software, as provided in detail below. The pipetter may be driven by a belt and a series of pulleys coupled to at least one motor (not shown) in a known manner to translate the pipetter in the x- and y-directions (i.e., along the plane defined by the work surface). Additionally, the pipetter may be vertically translated as a unit, or a single channel within the pipetter may be individually vertically translated. In this way, the pipetter may simultaneously transfer multiple samples, a single sample, or one or more standards. Because the distance between successive vials of one vial type within the respective vial rack is not necessarily the same distance as another vial type or the distance between successive vessels within the vessel rack, the pipetter may be configured to include a variable channel-spread such that the array of channels may laterally expand and contract, as necessary, to accommodate the varying distances when aspirating and dispensing samples. One exemplary model of a fluid handling system 26 for use in the automated station 20 is the Freedom EVO platform offered by Tecan Group, Ltd. (Männedorf, Switzerland). Of course, other commercially available fluid handling systems suitable for use in the automated station 20 are possible as well.

Returning again to the automated station 20 shown in FIGS. 1 and 2, each module 22, 24, 28 may include a cabinet base structure 32, 34, 36 for providing storage of components, such as a computer 38 that is configured to provide a user interface 300 (FIG. 15), that is necessary for operation of the automated station 20. The cabinet base structures 32, 34, 36 may additionally or alternatively store consumable materials. Each cabinet base structure 32, 34, 36 may include wheels, such as caster wheels 40, for moving the respective module 22, 24, 28 from one location to another. Further, each cabinet base structure 32, 34, 36 may include one or more extendable and retractable legs 42 that move to a first position when the particular module 22, 24, 28 is rolled between locations and to a second position for engaging the floor to prevent further movement of the module 22, 24, 28.

In using the automated station 20, the modules 22, 24, 28 are positioned side-by-side and aligned such that a top portion of each cabinet base structure 32, 34, 36 extends collinear with the adjacent cabinet and forms a unitary working surface 44. While not specifically shown, the modules 22, 24, 28 may include one or more locking structures (not shown) that, once the modules 22, 24, 28 are properly aligned, resists individual movement of any one module 22, 24, 28 relative to the other modules 22, 24, 28.

The automated station 20 is configured to: (i) receive racks 46a, 46b, 46c having one or more vials 48a, 48b, 48c therein and each containing a biological fluid specimen; (ii) to receive racks 50 having one or more vessels 52, each sized and shaped for use with a particular off-line analytical instrument (not shown); (iii) to open the one or more vials 48a, 48b, 48c; (iv) to transfer a sample of the biological fluid specimen from each vial 48a, 48b, 48c to a separate one of the vessels 52; (v) to close the one or more vials 48a, 48b, 48c; and (vi) to transfer the racks 46a, 46b, 46c, 50 of vials 48a, 48b, 48c and vessels 52 away from the automated station 20.

The racks 46a, 46b, 46c, 50 may be constructed of a metallic or polymeric material having a linear array of vertical openings along its length, the vertical openings being sized to receive and retain one vial 48a, 48b, 48c or vessel 52, respectively. As specifically shown, a smaller vial rack (indicated with number 46a) is configured to retain ten 45 mL vials (indicated with number 48a), a larger vial rack (indicated with number 46b) is configured to retain five 90 mL vials (indicated with number 48b), a smaller saliva vial rack (indicated with number 46c) is configured to retain ten saliva vials (indicated with number 48c), and the rack 50 is configured to retain ten vessels 52. However, the number of vessels 52 and vials 48a, 48b, 48c retained by the respective racks 50, 46a, 46b, 46c shown herein should not be considered to be limiting. To accommodate the difference in volume of the various vial-types, the width of the vial rack 46a, 46b, 46c may be adjusted accordingly, e.g., the vial racks 46a, 46c for the 45 mL vials 48a and the saliva vials 48c are narrower than the vial rack 46b for the larger 90 mL vials 48b.

The vials racks 46a, 46b, 46c may include a toothed surface 57 (FIG. 3B) on at least one lengthwise outer wall, which is configured to assist moving the rack 46a, 46b, 46c within the automated station 20, as will be described in greater detail below.

Movement of the racks 46a, 46b, 46c, 50 within the load module 22 may be accomplished with two conveyers: a first vial conveyer 54 and a first vessel conveyer 56. Each conveyer 54, 56 includes a belt 58, 60 that is operably associated with rollers (not shown) and a motor (not shown) that may be controlled by a computer, as described below. The belt 58 of the first vial conveyer 54 includes one or more pusher walls 62 extending radially outwardly therefrom for abutting and advancing one or more vial racks 46a, 46b, 46c from an input end 64 to an end that is adjacent to the transport path 30. The first vial conveyer 54 is flanked by rails 66 and alignment walls 68. The rails 66 may be an elevated portion of the working surface 44 on which the vial racks 46a, 46b, 46c may slide. The alignment walls 68 are spaced by the length of the vial racks 46a, 46b, 46c so as to align the vial racks 46a, 46b, 46c along the first vial conveyer 54.

The belt 60 of the first vessel conveyer 56 includes a plurality of walls 70 radially extending from the belt 60 and spaced to receive a single vessel rack 50 and to advance the vessel rack 50 from an input end 72 to an end that is adjacent to the transport path 30. Like the first vial conveyer 54, the belt 60 of the first vessel conveyer 56 is flanked by alignment walls 74 that are spaced by a length of the vessel rack 50 so as to align the vessel rack 50 along the first vessel conveyer 56. While not specifically shown, the alignment walls 74 may include one or more optional spacer plates for fitting and conveying vessel racks 50 that are shorter than the examples illustrated herein.

Each conveyer 54, 56 terminates at the transport path 30 with a wall 76, 78, respectively. With respect to the first vial conveyer 54, a push bar 80 coupled to a belt (not shown) extends through the wall 76 and is configured to engage an outer side wall of the rack 46a, 46b, 46c and to translate that vial rack 46a, 46b, 46c along the wall 76, i.e., a vial rack path of the transport path 30. Translation of the vial rack 46a, 46b, 46c along the transport path 30 continues between the wall 76 and a barrier wall 82, which further aids in aligning and guiding the vial rack 46a, 46b, 46c along the transport path 30 and into a capper/decapper assembly 84. Because the width of the 90 mL vial rack 46b is greater than the width of the illustrated 45 mL vial rack 46a or of the saliva vial rack 46c, the barrier wall 82 may include a removable spacer plate 83 to accommodate the varying size racks. More specifically, when the spacer plate 83 is affixed to the barrier wall 82 (such as by bolts or screws), then the transport path 30 is configured to receive the more narrow 45 mL vial racks 46a or saliva vial racks 46c; however, when the spacer plate 83 is removed, then the transport path 30 is configured to receive the larger 90 mL vial racks 46b. As shown, the wall 76 and the barrier wall 82 (as well as the spacer plate 83) may be segmented at the borders between the various modules 22, 24, 28 in order to allow for mobility of the modules 22, 24, 28.

As the vial rack 46a, 46b, 46c continues between the wall 76 and the barrier wall 82 (or the spacer plate 83, if necessary), the vial rack 46a, 46b, 46c engages a toothed belt 86 of the transfer module 24 having a plurality of teeth spaced to align with and to receive the toothed surface 57 (FIG. 3B) of the vial rack 46a, 46b, 46c. The toothed belt 86 may extend up to or at least partially into the load module 22 such that as the push bar 80 translates the vial rack 46a, 46b, 46c between the barrier wall 82 (or spacer plate 83 as appropriate) and the wall 76 toward the toothed belt 86, which engages the vial rack 46a, 46b, 46c and further translates the vial rack 46a, 46b, 46c into the capper/decapper assembly 84. While not specifically shown, the toothed belt 86 may be enclosed by a wall or housing having a slot through which the plurality of teeth extends.

The vessel rack 50 is transferred between the load module 22 and the transfer module 24 in a similar manner. Specifically, a push bar 85 (FIG. 2) may extend through the wall 78 and is configured to abut an edge of the vessel rack 50 and translate that vessel rack 50 along the wall 78, i.e., along vessel rack path of the transport path 30, to a first pusher belt 90. Said another way, the pusher bar 85 (FIG. 2) translates the vessel rack 50 to the first pusher belt 90 and then retracts to a rest position, ready to receive another vessel rack 50. A tab 91 (FIG. 2) extending radially from the first pusher belt 90 abuts the edge of the vessel rack 50 and further translates the vessel rack 50 to the capper/decapper assembly 84. Again, while not specifically shown, the first pusher belt 90 may be enclosed by a wall or housing having a slot through which the tab 91 (FIG. 2) extends.

While not specifically shown, one or more sensors may be positioned along the transport path 30 to determine and indicate proper alignment of the racks 46a, 46b, 46c, 50 with respect to the capper/decapper assembly 84 and along the transport path 30. Suitable sensors may include optical or laser sensors, for example.

Figure 3A:
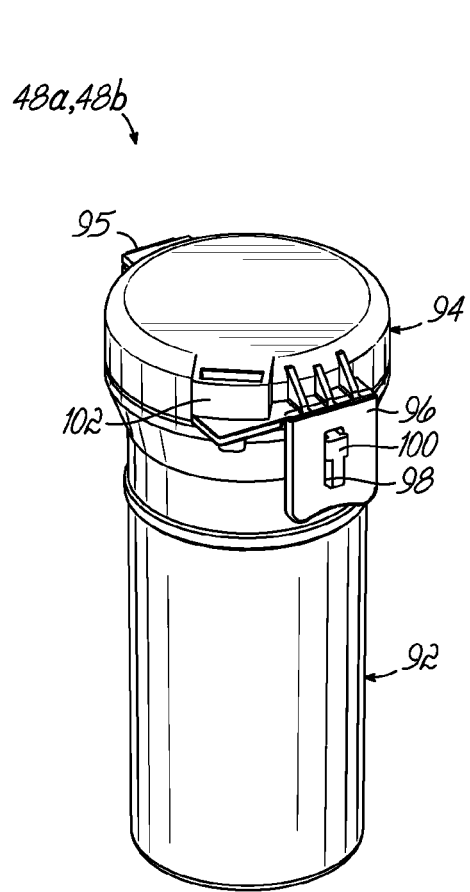
FIG. 3A is a perspective view of one exemplary vial for use with the automated vial capper/decapper station of FIG. 1.
Figure 3C:
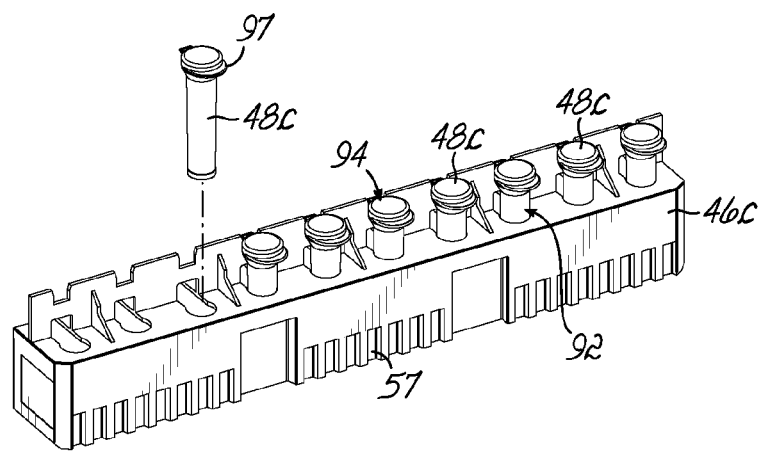
FIG. 3C is a perspective view of another exemplary vial and a vial rack for use with the automated vial capper/decapper station of FIG. 1.

The details of the capper/decapper assembly 84 and embodiments of suitable vials 48a, 48b, 48c for use therewith are now described with reference to FIGS. 3A-3C. One exemplary type of vial 48a, 48b may be, for example, the 45 mL or 90 mL flip-top vials commercially-available from Capitol Vial (Auburn, Ala.). Another exemplary type of vial 48c may be the 3 mL saliva flip-top vial that is also commercially-available from Capitol Vial. These vials 48a, 48b, 48c may include an open-ended vial body, or a container 92, having a lid, or flip-top cap 94, that is coupled to the container 92 by a hinge 95. In one embodiment, the hinge 95 may be provided on a strap that connects the cap 94 to the container 92. Indeed, in some embodiments, the container 92, the cap 94, and the hinge 95 may be constructed as an integral, or unitary, structure from a polymeric material, such as polypropylene. The cap 94, when pressed onto an opening of the container 92, forms at least one fluid-tight seal with the container 92. However, in some embodiments, sealing or tamper evidence tape (not shown) may be used on the vials 48a, 48b, 48c.

The cap 94 of the 45 mL and 90 mL vials 48a, 48b may include a locking tab 96 that extends from the cap 94 and includes an opening 98 therein configured to receive a locking strip 100 formed on an outer surface of the container 92. When the locking tab 96 engages the locking strip 100, the engagement prevents inadvertent and/or premature decapping and opening of the vial 48a, 48b. Because the illustrative saliva vial 48c (FIG. 3C) does not include the locking tab 96 of the other vial types, the cap 94 of the saliva vial 48c may include an enlarged tab 97 to facilitate opening, as described below.

Furthermore, the cap 94 of the 45 mL vials 48a may also include a tamper-resistant tab 102 that engages an irreversible chain lock (not shown) extending upwardly from the container 92. In use, the tamper-resistant tab 102 receives the irreversible chain lock during or shortly after the molding process so that the vial 48a remains locked and sealed until the biological fluid specimen is ready for deposit. This reduces the likelihood of fraud or pre-contamination during drug-of-abuse testing. One suitable vial for use in the automated station 20 (FIG. 1) is fully described in U.S. Pat. No. 5,133,470, owned by the common assignee, and incorporated herein by reference in its entirety.

While not specifically shown, several additional features may also be included with the vials 48a, 48b, 48c such as a bar code or radiofrequency identification ("RFID") antenna for sample tracking, a temperature indicator strip, and one or more labels for displaying specimen indicators, for example, biohazard, as required by laws and/or regulations. It would be understood that while certain ones of the vials 48a, 48b, 48c are illustrated and described herein as having certain features, any combination of features may be incorporated into a vial of a particular or desired volume and the features need not be limited to the exemplary feature combinations described herein.

While not shown in great detail, the vessels 52 (FIG. 2) may be, for example, any open-top vessel or a capped vessel, such as the 5-up or 10-up Analyzer Cup Strips that are commercially-available from Capitol Vial (Auburn, Ala.). Yet other alternatives may include a screw-top cap, a piercable septa, or other closure device configured to prevent evaporation of the sample or standards added thereto. The vessels 52 (FIG. 2) may desirably, but not necessarily, be configured to contain a smaller volume than the vials 48a, 48b, 48c. The vessels 52 (FIG. 2) may be constructed from a polymeric structure, glass, quartz, or other material as required by the particular analyzer for which the sample is being prepared.

Figure 3B:
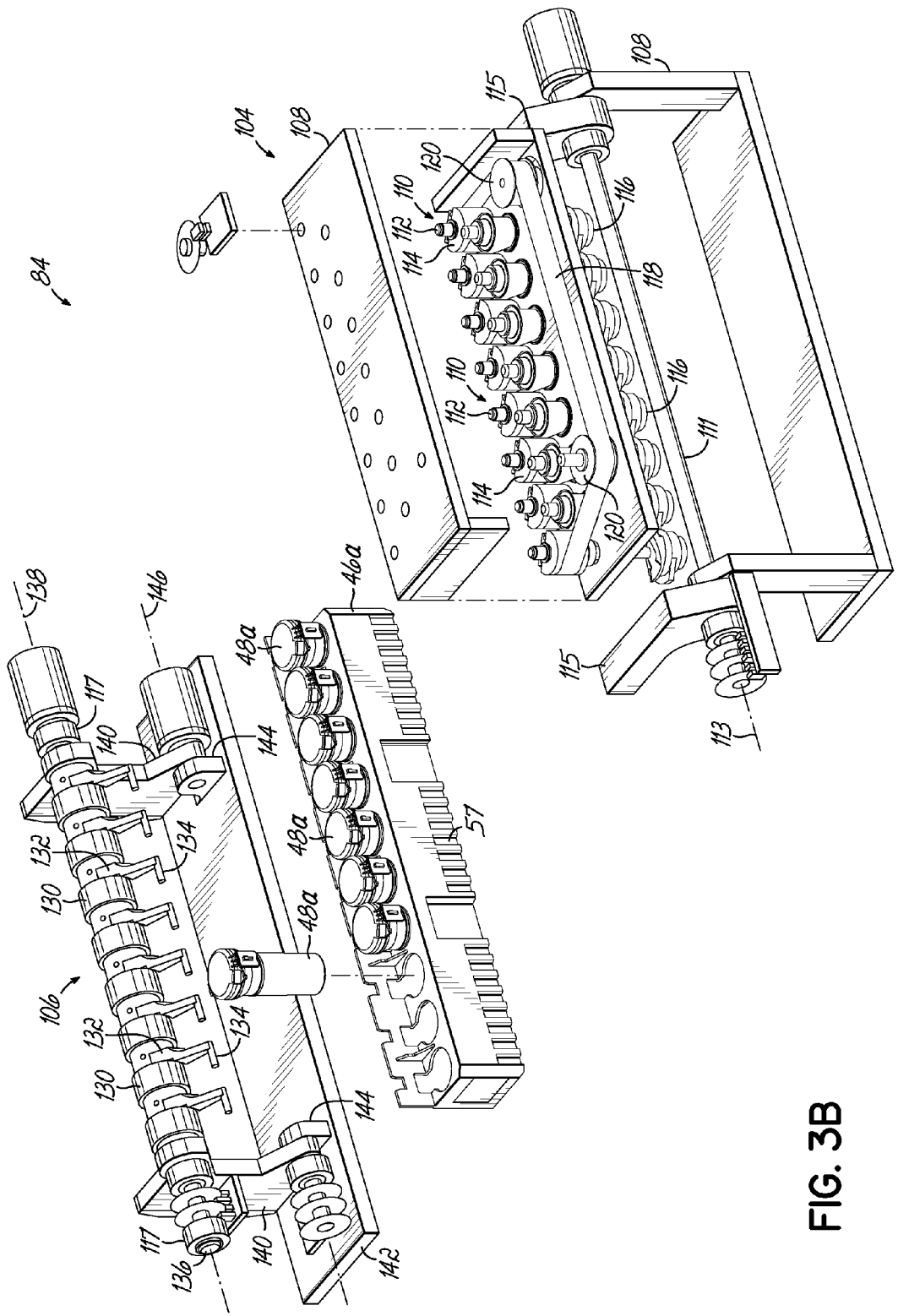
FIG. 3B is a perspective view of a capper/decapper assembly of the automated vial capper/decapper station of FIG. 1.
Figure 4:
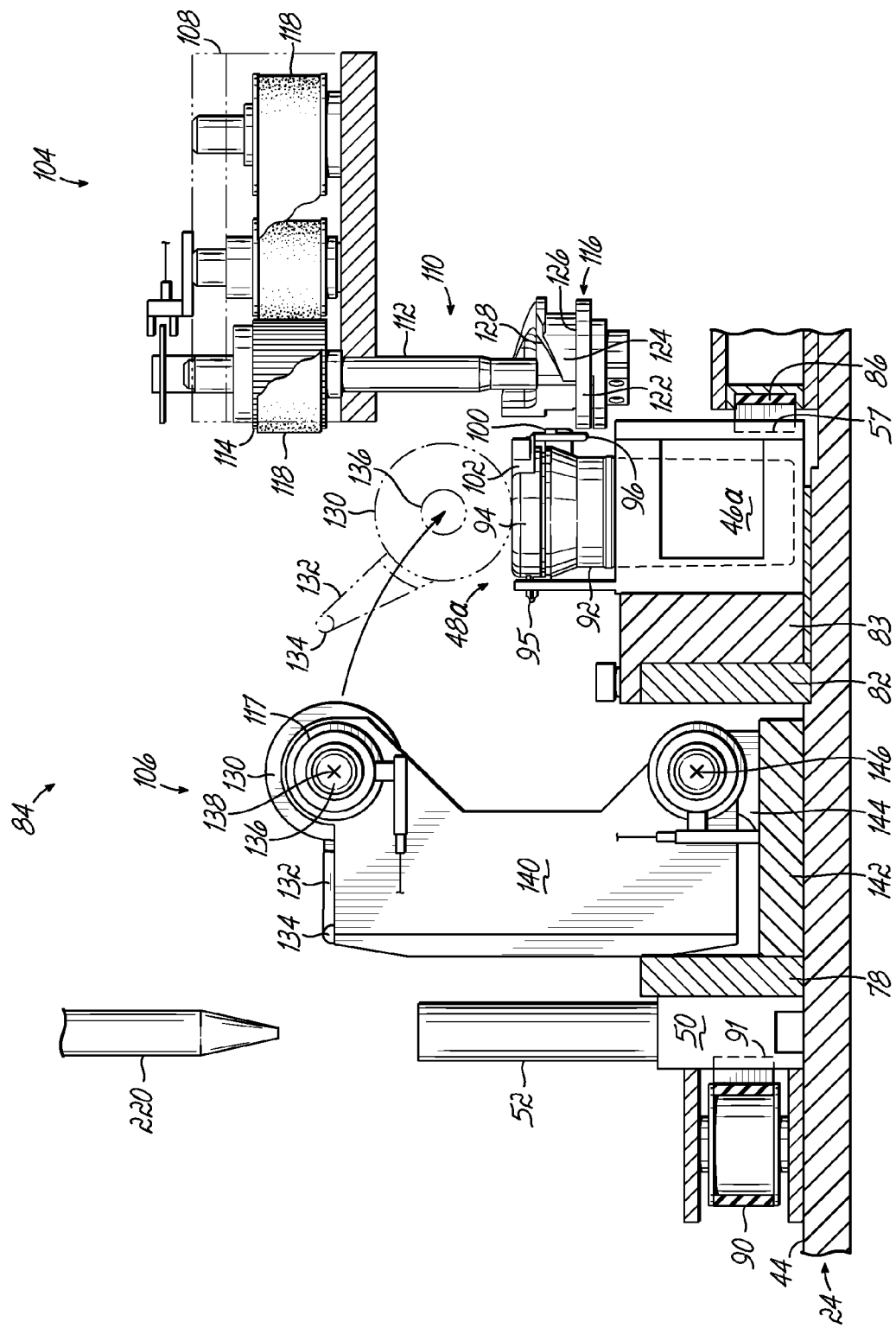
FIGS. 4 and 4A are side elevational views of the capper/decapper assembly of FIG. 3B in use with a small vial rack (FIG. 4) and a large vial rack (FIG. 4A).
Figure 4A:
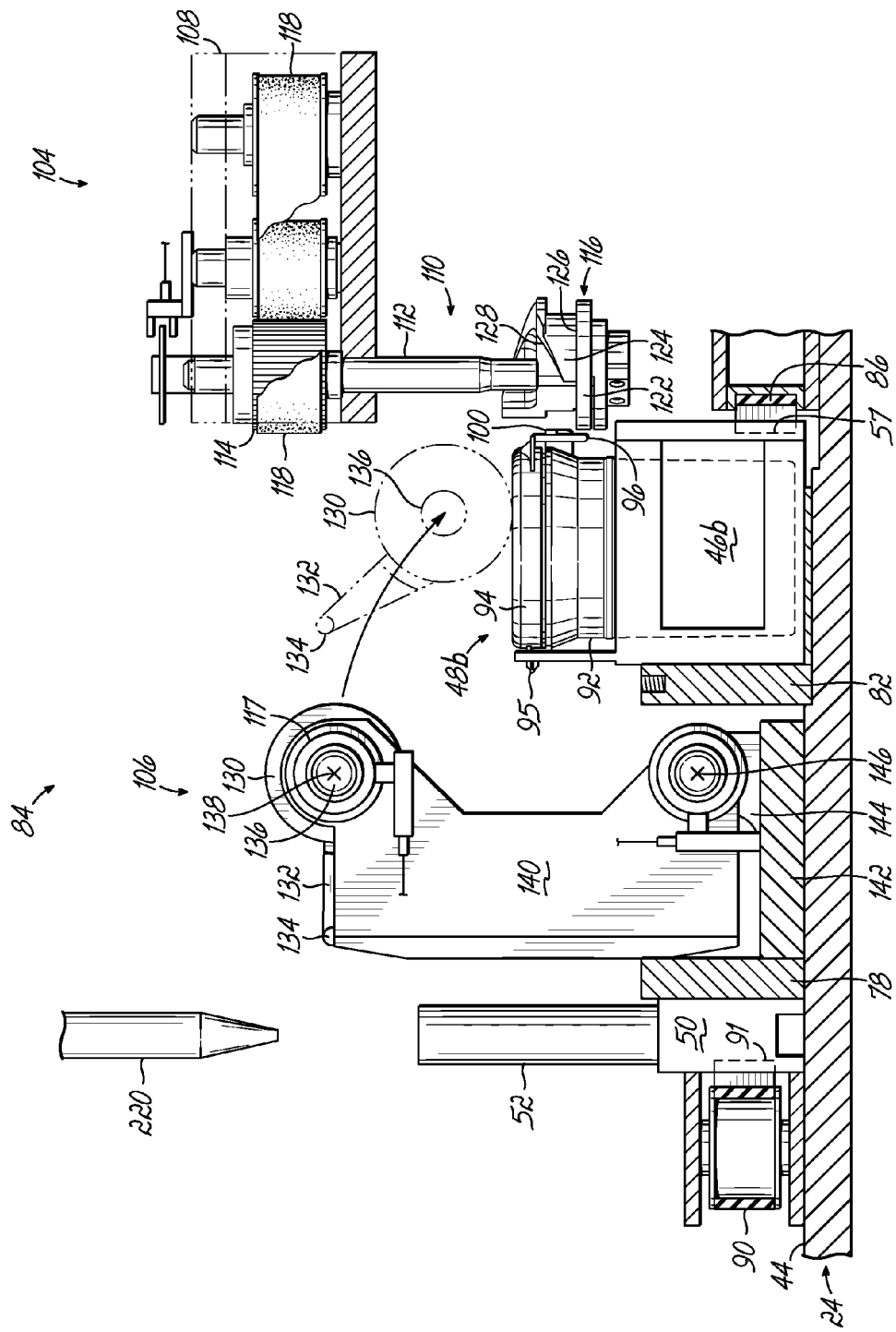

With reference now to FIG. 3B, the details of the vial capper/decapper assembly 84 are described in detail as including a spindle cam assembly 104 and a rotating arm assembly 106. The spindle cam assembly 104 includes a housing 108 surrounding a plurality of spindles 110 that are arranged linearly. While not necessary, the number of spindles 110 may be equal to the number of channels of the pipetter of the fluid handling system 26 (FIG. 1). As illustrated, eight spindles 110 are used and would correspond to an 8-channel pipetter.

The housing 108 further includes a rod 111 that extends therethrough and in a direction that is substantially parallel to the linearly arranged plurality of spindles 110, and defining a rotational axis 113. At least one closure arm 115 (two closure arms 115 are shown) is coupled to a lateral end of the rod 111 and extends radially therefrom such that rotation of the rod 111 about the rotational axis 113 rotates the closure arm 115. As will be described below, the closure arm 115 aids in capping and sealing the vials 48a, 48b, 48c.

Figure 4B:
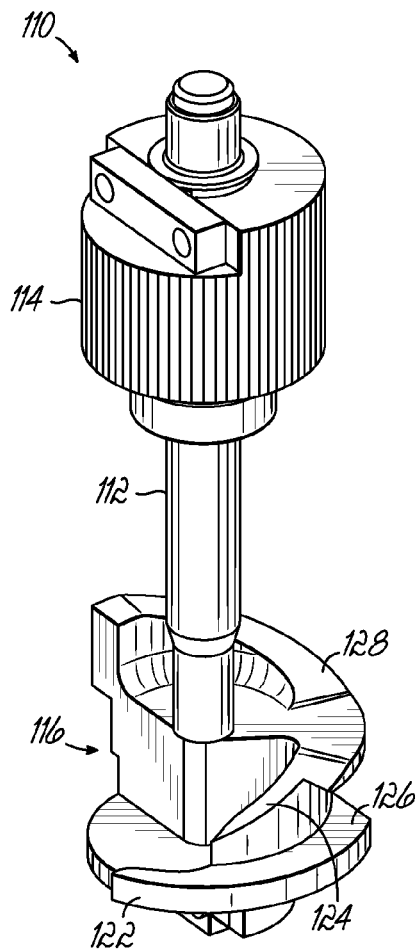
FIG. 4B is an enlarged perspective view of a spindle of the capper/decapper assembly of FIG. 3B.

Turning now to the plurality of spindles 110, with further reference to FIGS. 3B and 4B, each spindle 110 includes a central rotatable shaft 112, an upper gear portion 114, and a lower vial engagement portion 116. While the spindle 110 may be constructed as a unitary structure, the specific illustrative embodiment is constructed with the central rotatable shaft 112 of a metallic or polymeric material and molded polymeric gear and vial engagement portions 114, 116. The gear and vial engagement portions 114, 116 are slipped over appropriate ends of the rotatable shaft 112 and bolted to a flat face of the shaft 112 or, alternatively, retained by friction fit or an adhesive.

The gear portion 114 is configured to engage a belt 118 that is driven by a plurality of pulleys 120 and a motor (not shown). The belt 118 is configured to simultaneously rotate all spindles 110 of the linear array in order to simultaneously decap all vials 48a, 48b, 48c within the loaded rack 46a, 46b, 46c.

The vial engagement portion 116 includes two projections, such as two fingers in one embodiment, positioned radially outwardly from the rotatable shaft 112. The first finger 122 is positioned below or distally of the second finger 124 and expands circumferentially to a generally planar body 126. The second finger 124 expands circumferentially to a cam surface 128, which is inclined relative to the shaft 112. The first and second fingers 122, 124 are axially offset such that the second finger 124 resides proximally or above the generally planar body 126 of the first finger 122 and would thus engage the vial 48a, 48b, 48c after the first finger 122 as the spindle 110 is rotated in a clockwise direction.

Referring still to FIG. 3B, the rotating arm assembly 106 includes a plurality of rollers 130, where the number of rollers 130 is equal to the number of spindles 110 of the spindle cam assembly 104. Each roller 130 includes a radially-extending lid engaging arm 132 having a finger 134 at a distal end of the engaging arm 132 and extending angularly therefrom. The rollers 130 are spaced apart from each other and coupled to or otherwise supported by a rod 136 along a first rotational axis 138 so that all rollers 130 may simultaneously rotate. The fingers 134 of the engaging arm 132 are configured to engage the cap 94 (FIG. 3A) or, more particularly, the locking tab 96 (FIG. 3A) or the enlarged tab 97 (FIG. 3A) of the cap 94 (FIG. 3A), of the respective vial 48a, 48b, 48c as described in detail below. The rod 136 is coupled to a support, one embodiment of which is a pair of parallel plates 140 that are, in turn, rotatably coupled at a base 142 about plate supports 144 defining a second rotational axis 146. Though not shown, the rod 136 and the plate supports 144 may be coupled to one or more gears and motors for operation of the plates 140 and rollers 130 as described in detail below.

Figure 12:
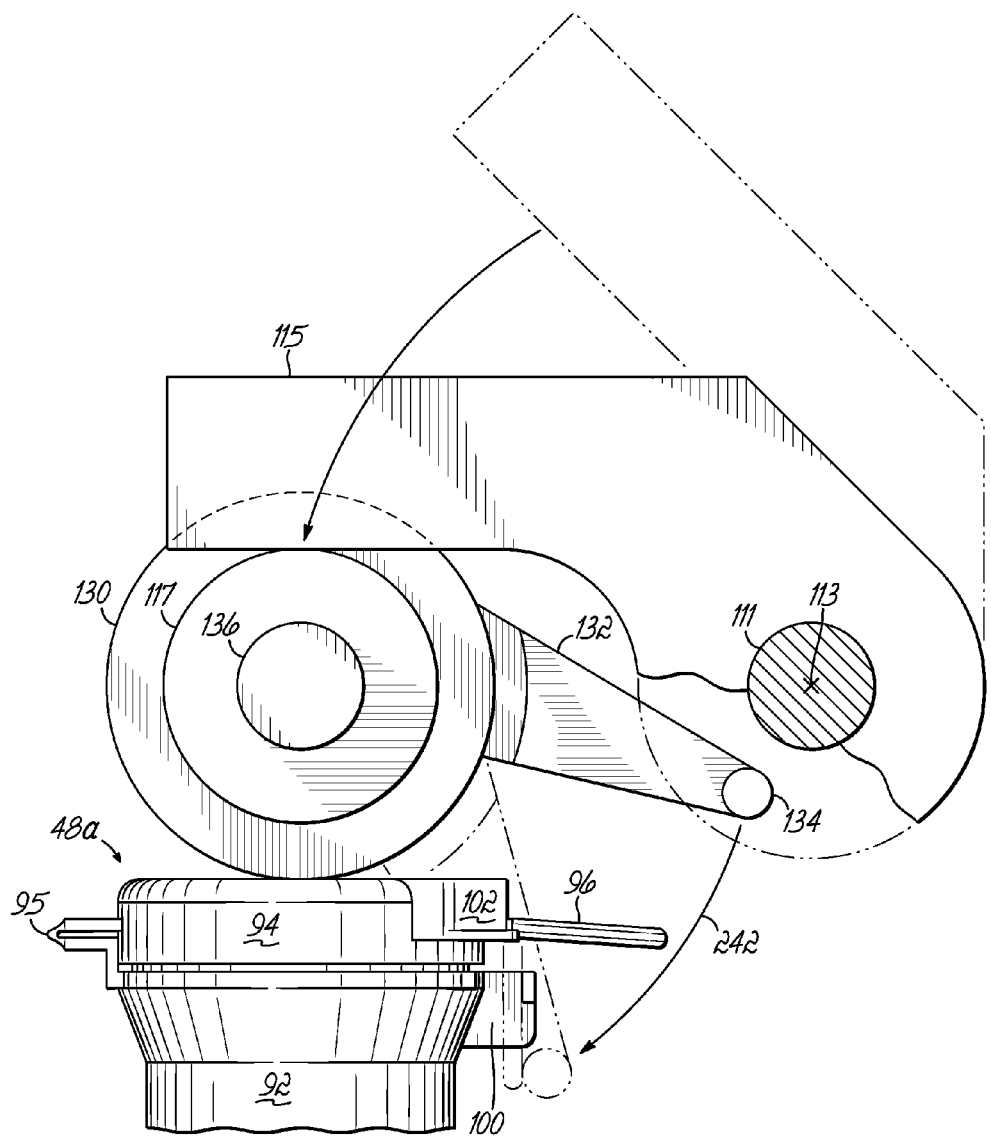
FIGS. 12 and 13 are side elevational views of an exemplary process of capping the vial with the capper/decapper assembly of FIG. 3B.
Figure 13:
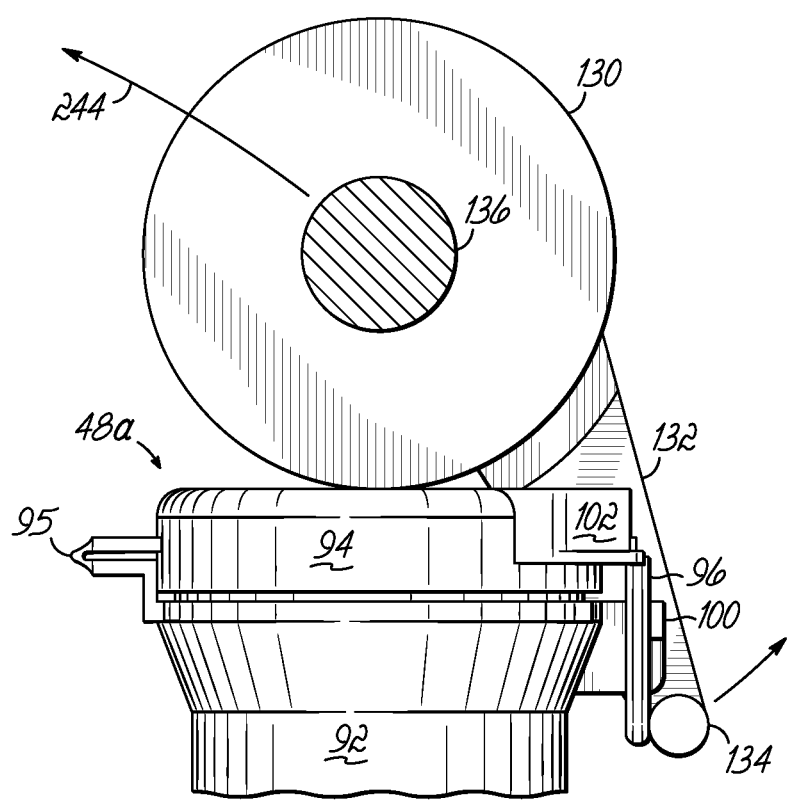
Figure 14:
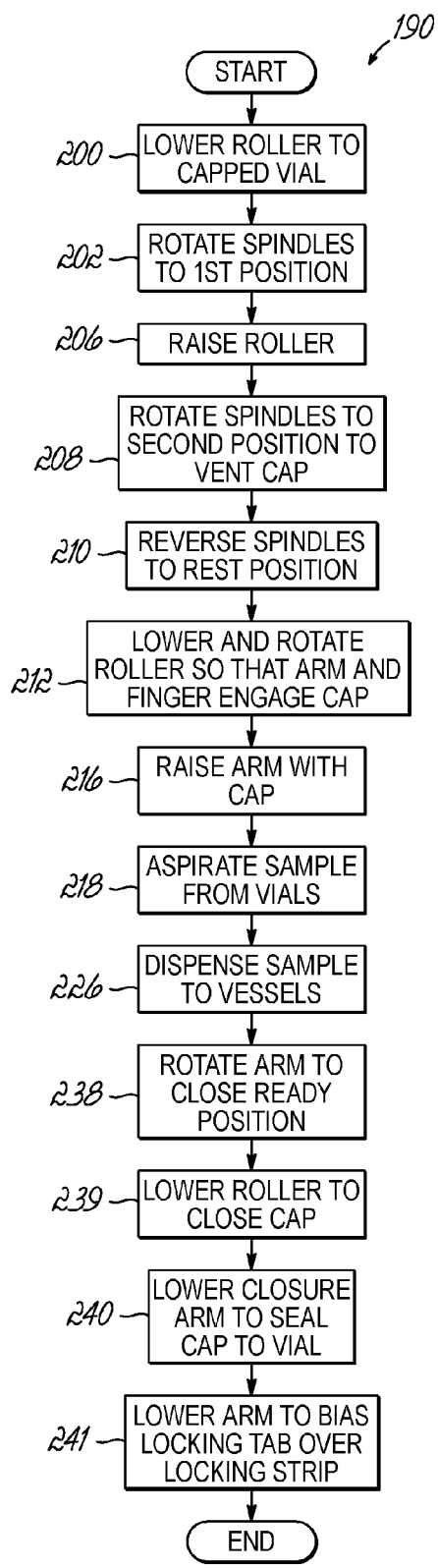
FIG. 14 is a flowchart illustrating the exemplary process for decapping, opening, and capping the vial, shown in FIGS. 5-13.

FIGS. 5-13 illustrate one method of using the capper/decapper assembly 84 to transfer a sample of the biological fluid specimen from those vials 48a, 48b having the locking strip 100. Specifically, these figures illustrate the opening, sampling, and closing of the locking strip 100 and cap 94 of one vial 48a, 48b. Further, reference is made to the flowchart 190 in FIG. 14 illustrating a process flow according to one embodiment of the present invention. One of ordinary skill will readily appreciate that while the process is illustrated for one vial 48a, 48b, because all spindles 110 and all rollers 130 are coupled together and move in unison, all vials 48a, 48b within the loaded vial rack 46a, 46b are simultaneously decapped, the samples aspirated and dispensed to the vessels 52 (FIG. 2), and all vials 48a, 48b recapped within the capper/decapper assembly 84.

In FIGS. 5 and 5A, the vial 48a, 48b (for illustrative convenience, only vial 48a is shown and referenced with respect to FIGS. 5-13) is aligned, or registered, with the corresponding spindle 110. Further, the alignment is such that the corresponding roller 130, when lowered, will be positioned substantially above the capped vial 48a.

Figure 6:
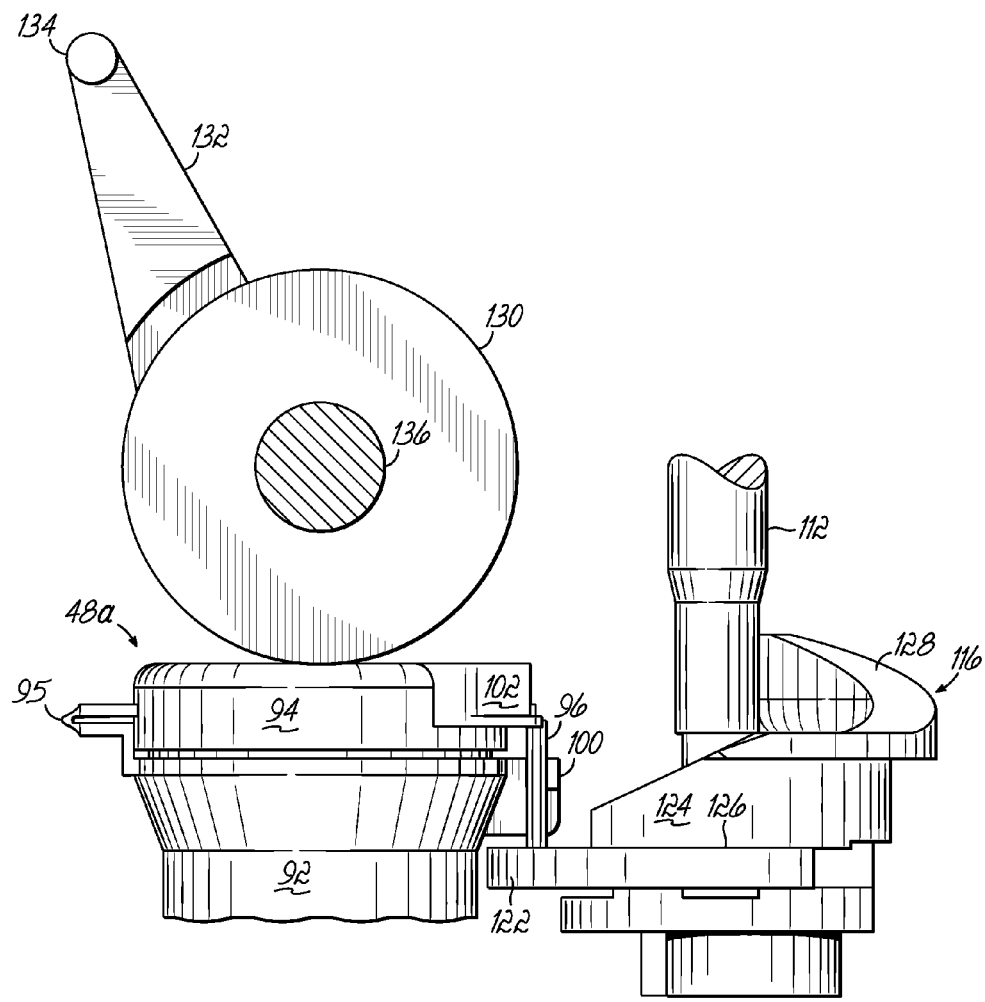
Figure 6A:
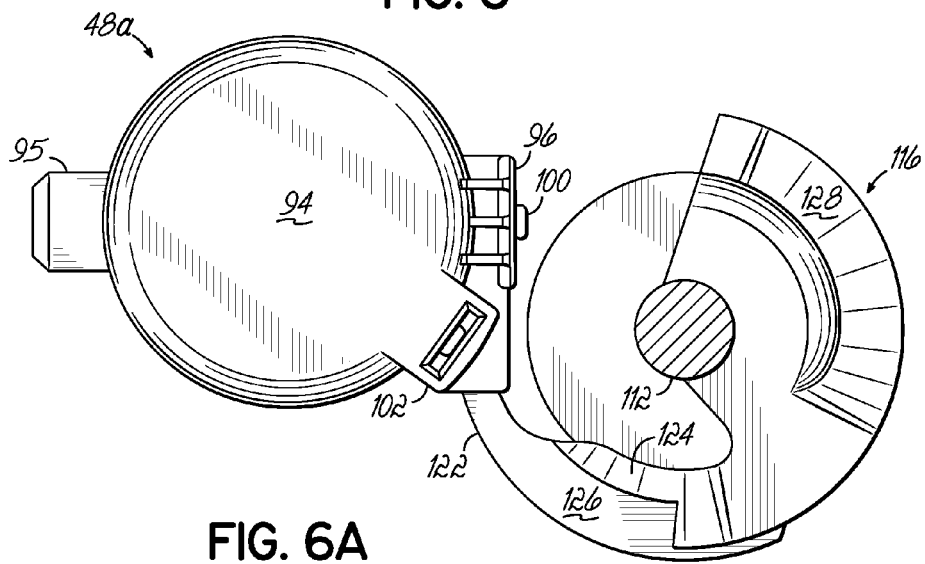
Figure 7:
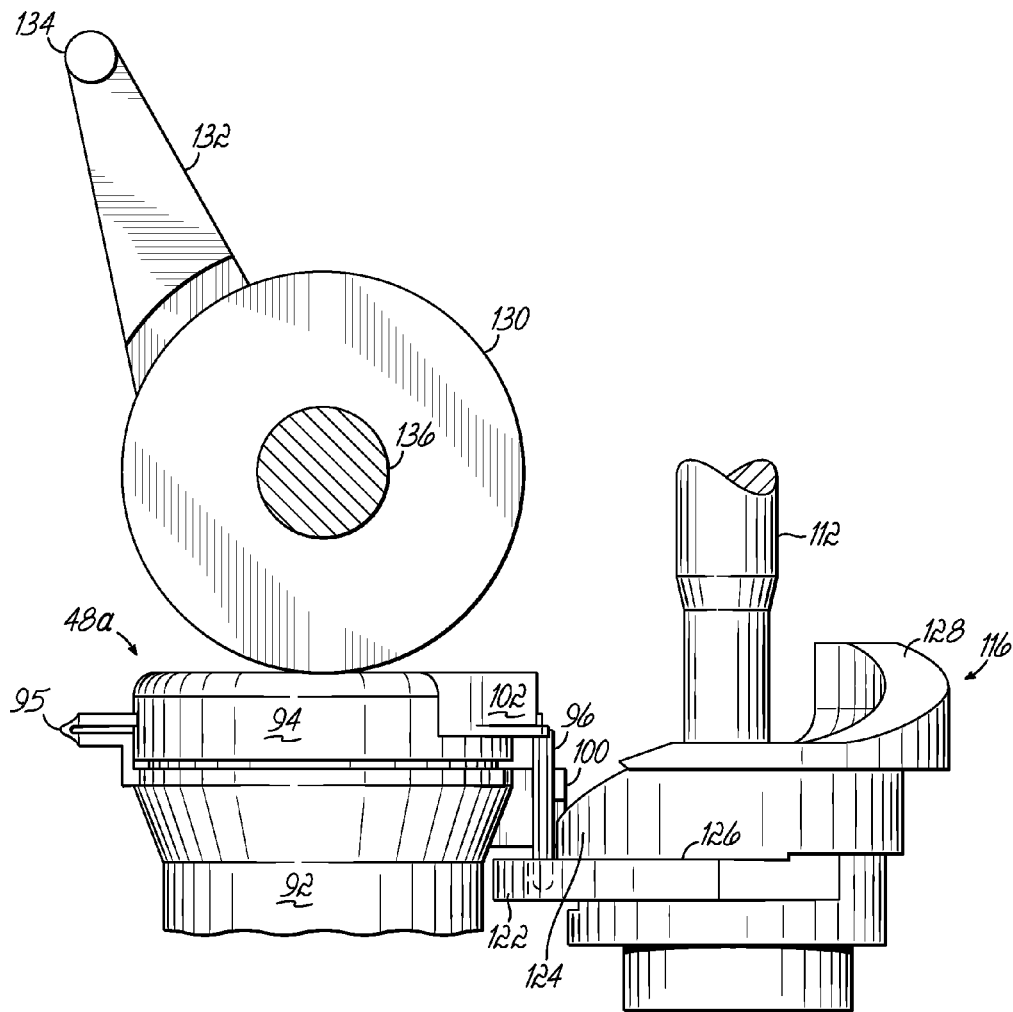
Figure 7A:
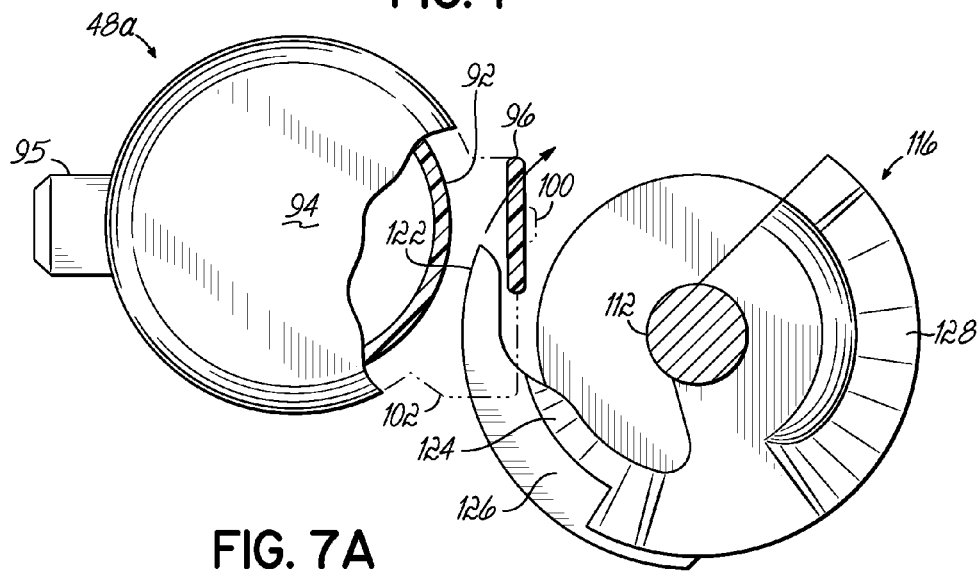

In FIGS. 6 and 6A, the roller 130 is lowered to rest atop the closed cap 94 of the vial 48a (block 200 of FIG. 14). The lowered roller 130 is beneficial in preventing the premature opening of the cap 94 and/or removal of the vial 48a from the rack 46a, 46b (FIG. 2); however, this may not be necessary and should not be considered to be limiting. The spindle 110 (FIG. 3B) may also rotate, at least partially, as shown, to a position configured to engage the vial 48a.

Figure 8:
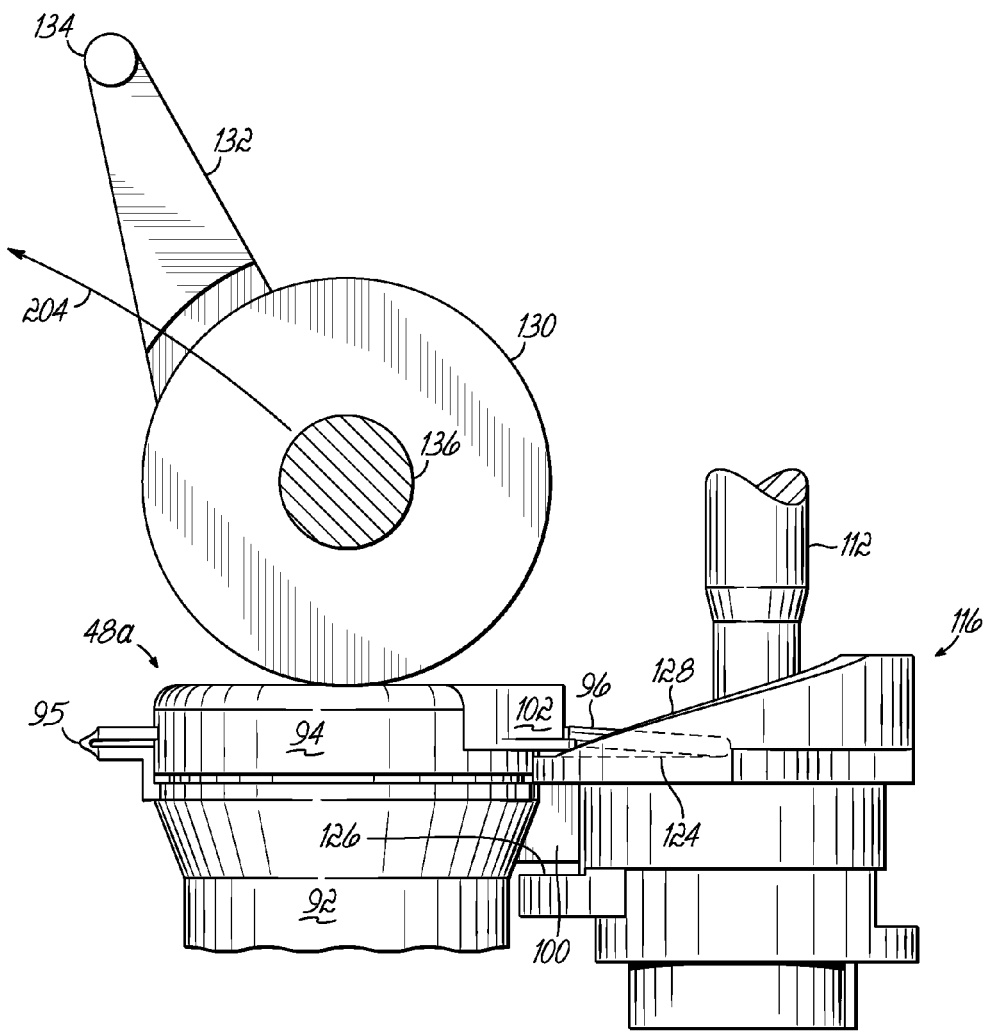
Figure 8A:
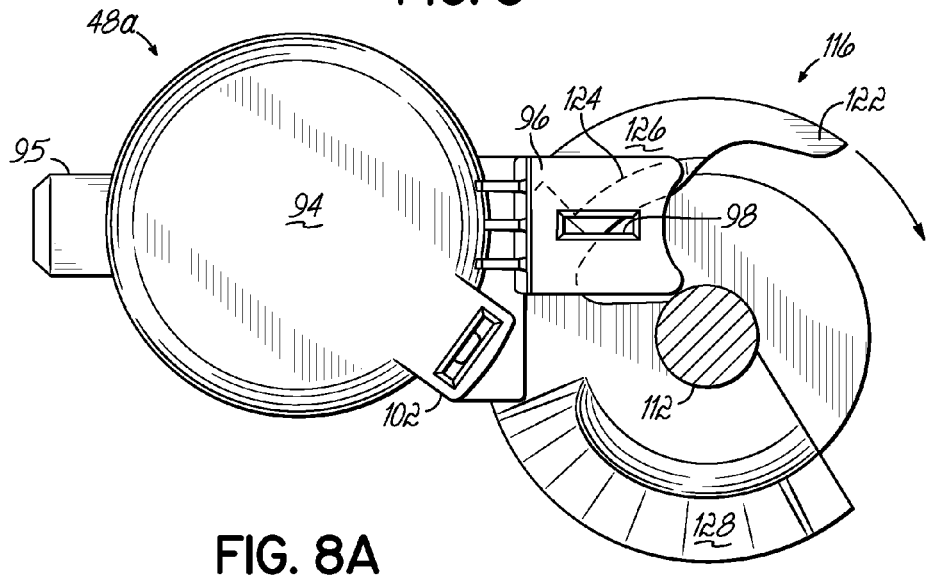

FIGS. 7, 7A, 8, and 8A illustrate rotation of the spindle 110 (FIG. 3B) from a rest position to a first position such that the first finger 122 slips between the locking tab 96 and the container 92 and below the locking strip 100. Because the width of the first finger 122 increases or expands circumferentially, continued rotation of the spindle 110 biases the locking tab 96 away from the locking strip 100 (block 202) and the vial 48a is prepared to be decapped as shown in FIGS. 8 and 8A.

In FIG. 8, the plates 140 (FIG. 3B) of the rotating arm assembly 106 (FIG. 3B) are rotated about the second rotational axis 146 (FIG. 3B) to raise the roller 130 away from the cap 94, as indicated by the arrow 204 (block 206).

Figure 9:
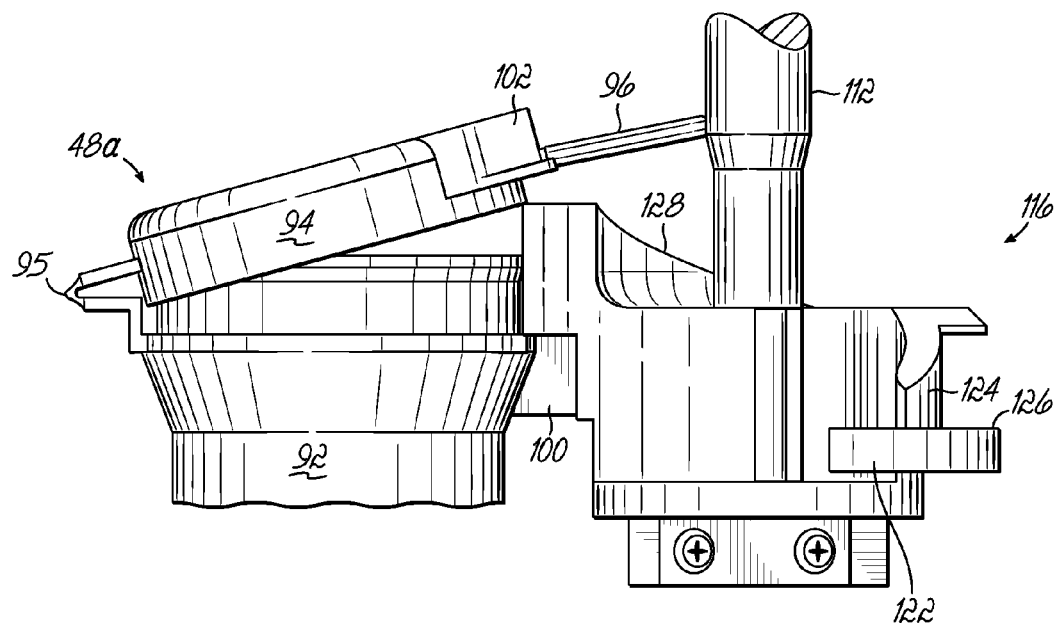
Figure 9A:
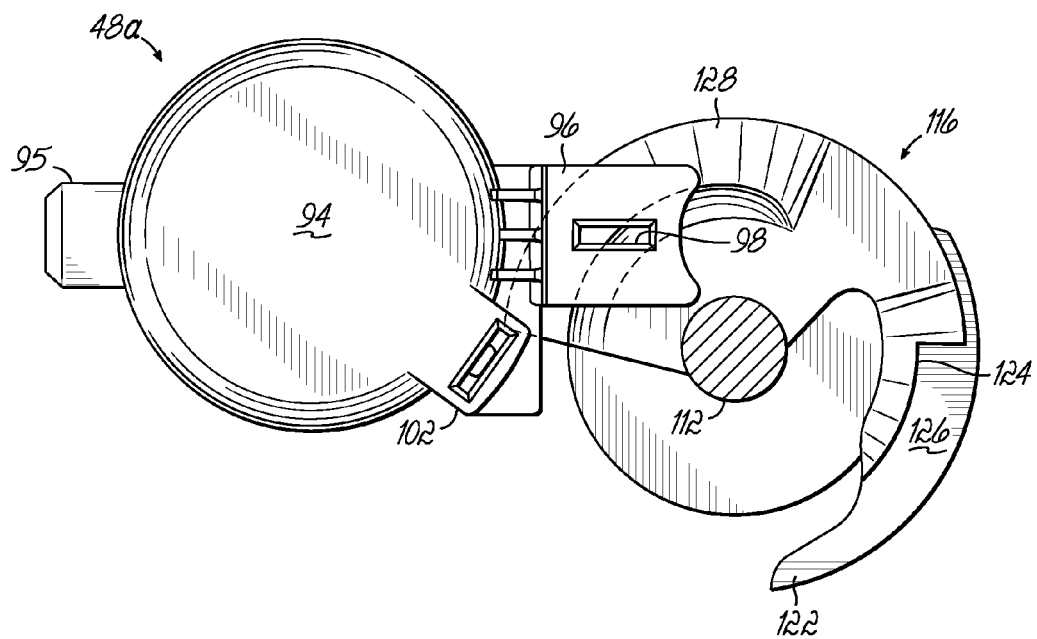

In FIGS. 9 and 9A, the spindle 110 (FIG. 3B) is further rotated in the clockwise direction to a second position such that the second finger 124 slips between the biased/opened locking tab 96 and the container 92 and above the locking strip 100 (FIG. 3B). The tip end of the second finger 124 may breach, or score, any sealing or tamper evidence tape that may be present on the vial 48a, 48b. Continued rotation of the spindle 110 causes the cam surface 128 to engage and bias the cap 94 upwardly, thereby venting the cap 94 (block 208). Said another way, rotation of the cam surface 128 associated with the second finger 124 breaches the at least one fluid-tight seal between the container 92 and the cap 94 by applying an upwardly directed force onto the closed cap 94. As illustrated, the cam surface 128 may engage a portion of the tamper-resist tab 102 for biasing the cap 94 upward; however, it would be understood that the cam surface 128 may engage any portion of the tab or other protruding portion of the cap 94.

While not specifically shown, the spindle 110 (FIG. 3B) may then rotate, counter-clockwise, to the rest position such that the first and second fingers 122, 124 do not interfere with further opening of the cap 94 (block 210).

Figure 10:
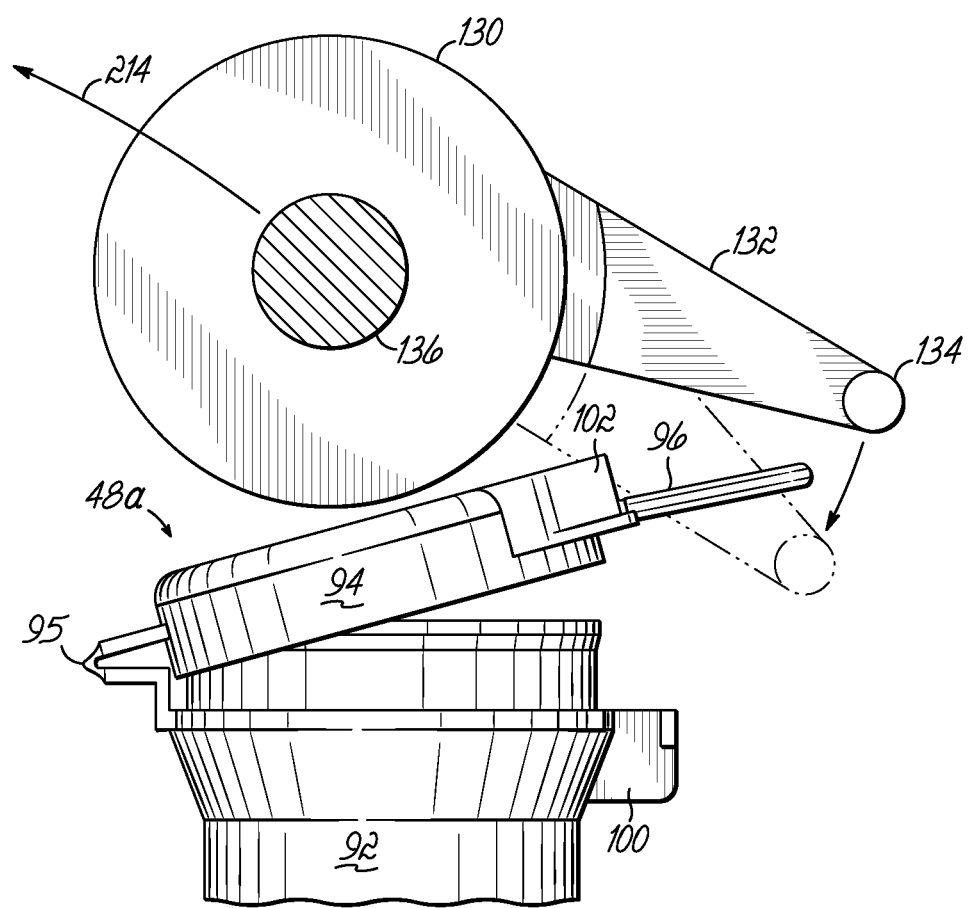
FIGS. 10 and 11 are side elevational views of an exemplary process of opening the vial and aspirating a sample from a biological fluid specimen contained within the vial.
Figure 11:
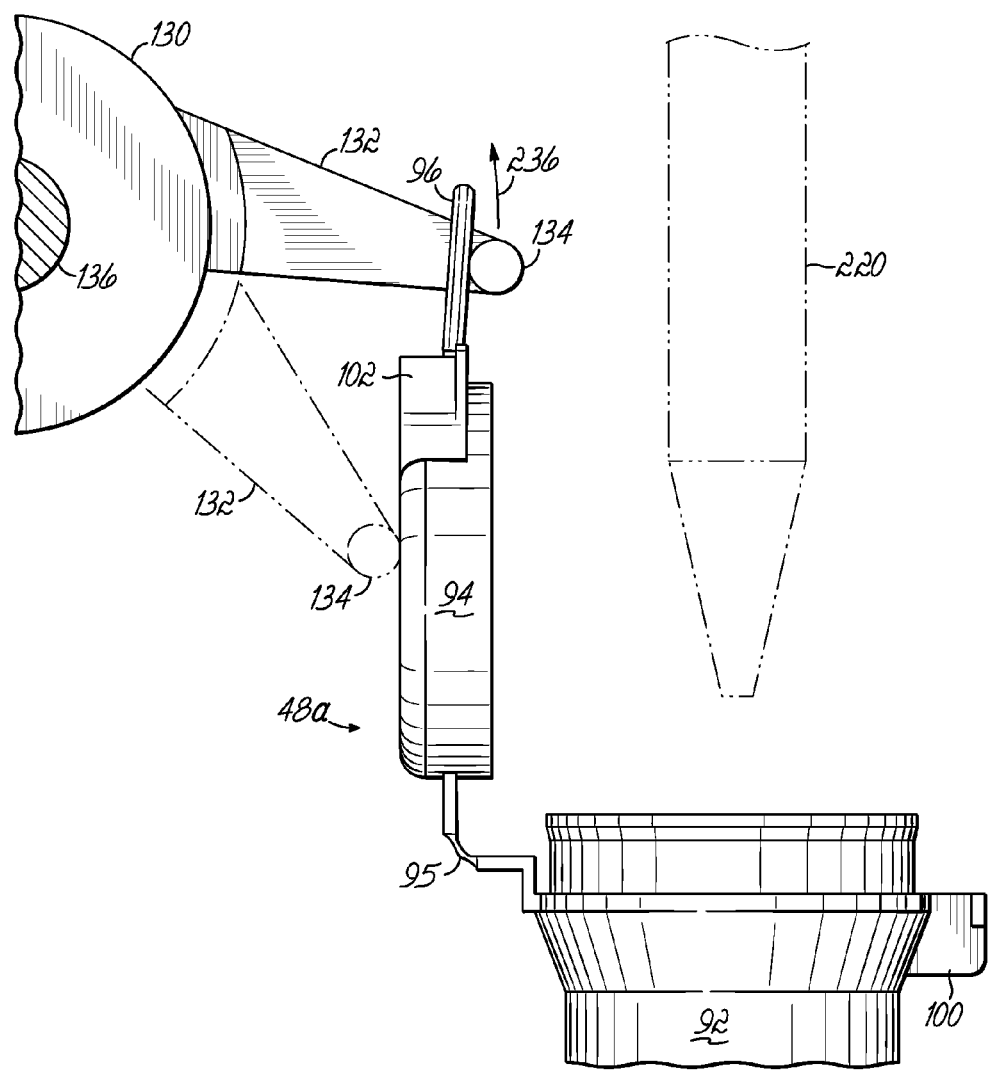

Opening of the cap 94 is shown in FIGS. 10-11 and includes rotating the plates 140 (FIG. 3B) of the rotating arm assembly 106 (FIG. 3B) about the second rotational axis 146 (FIG. 3B) toward the vial 48a while the arm 132 of the roller 130 is slightly elevated (shown in solid in FIG. 10). As the plates 140 (FIG. 3B) continue rotating about the second rotation axis (FIG. 3B), the roller 130 continues to advance toward the vented cap 94 and is rotated about the first rotational axis 138 (FIG. 3B) such that the arm 132 is advanced around the now forwardly-extending locking tab 96. Continued rotation of the plates 140 (FIG. 3B) and the roller 130 places the arm 132 below the locking tab 96 (shown in phantom in FIG. 10). In this way, the finger 134 of the arm 132 is positioned to engage the locking tab 96 (block 212). It would be appreciated by those of ordinary skill in the art that, in order to eliminate or reduce the likelihood of contamination, the finger 134, the arm 132, or any other portion of the rotating arm assembly 106 should only contact the locking tab 96 or another external portion of the cap 94 and not contact any inner surface of the vial 28a, including an inner surface of the container 92 and an inner surface of the cap 94.

Once the rotating arm assembly 106 (FIG. 3B) engages the locking tab 96, the plates 140 (FIG. 3B) are rotated about the second rotational axis 146 (FIG. 3B) so as to rotate the roller 130 away from the vial 48a, thereby causing the arm 132 to pull the locking tab 96, and resultantly the attached cap 94, in the direction of the arrow 214 (block 216). After rotation is complete, the cap 94 is fully opened, as shown in FIG. 11.

FIG. 11 further illustrates the aspiration of a sample from the vial 48a (block 218). Aspiration of the sample includes activation of the one or more robotics associated with the pipetter (not shown) of the fluid handling system 26 (FIG. 1). The pipetter may be operable with disposable tips 220 or with washable tips, as desired. While not specifically shown, if washable tips are used, then the transfer module 24 (FIG. 1) may further include a wash station having at least one solvent for washing the tip and a liquid waste chute for receiving used solvent. As is shown, the pipetter utilizes disposable tips 220. Accordingly, the transfer module 24 (FIG. 1) may further include one or more drawers 222 (FIG. 1) for storing a supply of disposable tips 220 within tip racks 224 (FIG. 1).

With the appropriate tip 220 selected and loaded onto the pipetter, the tip 220 is directed to a position above the opened vial 48a (shown in phantom). The tip 220 is then lowered into the vial 48a such that an aliquot of the biological fluid specimen within the container 92 is aspirated into the tip 220. The tip 220 is then elevated out of the opened vial 48a and the pipetter is translated to a position that is above the vessel 52 (FIG. 3B). With the tip 220 so positioned, the tip 220 is lowered into the vessel 52 (FIG. 2) such that the sample is dispensed from the tip 220 and into the vessel 52 (FIG. 2) (block 226).

If desired, and in accordance with the particular biological fluid specimen, one or more reagents and/or internal standards may also be transferred to the vessel 52 (FIG. 2). Accordingly, the pipetter may be translated to a position above a standards station 228 (FIG. 2) containing the one or more quality control standards, internal standards, and/or reagents (hereafter "standards" 230). One channel of the pipetter, having an appropriate tip 220 coupled distally thereto, is lowered into the standard 230 (FIG. 2) such that an aliquot of the standard 230 (FIG. 2) is aspirated into tip 220. The aliquot of the standard 230 (FIG. 2) is then dispensed into the select vessel 52 (FIG. 2). It would be readily appreciated that different standards 230 (FIG. 2) may be stored within the standard station 228 (FIG. 2) such that different biological fluid specimens may be prepared by the automated station 20 (FIG. 1) in accordance with one or more assays. Standards 230 (FIG. 2) for testing urine, saliva, blood, and so forth, including buffers, wash solutions, diluents, detection reagents, and the like may be stored within the standards station 228 (FIG. 2) and dispensed into the appropriate vessel 52 (FIG. 2) before or after the vessel 52 (FIG. 2) receives the sample.

A fluid waste chute 232 (FIG. 2) that is fluidically coupled to a larger fluid container, a drain, or other appropriate fluid waste disposal unit (not shown) may be included within the standards station 228 (FIG. 2) for periodic rinsing the fluid handling system 26 (FIG. 1). This periodic rinsing may be necessary to reset the air gaps within the fluid handling system 26 (FIG. 1) and ensure pipetting accuracy. Disposable tips 220 may likewise be dispensed into a tip waste chute 234 (FIG. 2) to reduce cross contamination of biological fluid specimens, the standards 230 (FIG. 2), or other fluids within the transfer module 24 (FIG. 1).

With the sample transferred, the capper/decapper assembly 84 (FIG. 3B) is prepared to recap the vial 48*a* and transfer the vial rack 46*a*, 46*b* (FIG. 2) along the transport path 30 (FIG. 1) and away from the transfer module 24 (FIG. 1). One method of recapping the vial 48*a* is illustrated in FIGS. 11-13 with further reference to FIG. 14.

From the roller position that is shown in FIG. 11, the roller 130 is rotated about the first rotational axis 138 (FIG. 3B), as indicated by the arrow 236, to release the locking tab 96 and the cap 94. Continued rotation positions the arm 132 and the finger 134 behind the cap 94 (shown in phantom) and ready for closing the cap 94 (block 238). With the arm 132 and finger 134 so positioned, the plates 140 (FIG. 3B) are rotated about the second rotational axis 146 (FIG. 3B) to lower the roller 130 onto the cap 48*a*. Continued rotation advances the cap 94 onto the container 92, as is shown in FIG. 12 (block 239), and positions the arm 132 and the finger 134 beyond the cap 94 for rotation around the cap 94 to contact the locking tab 96. Still further rotation of the plates 140 (FIG. 3B) applies a downwardly-directed force onto the cap 94, thereby placing the cap 94 onto the vial 48*a*. One or more motors/pulleys (not shown) associated with the rod 111 are activated to rotate the rod 111 about the rotational axis 113 to lower the closure arms 115 onto the enlarged wheels 117 residing on the lateral ends of the rod 136. With continued rotation of the closure arms 115, sufficient downwardly-directed force is applied to the rod 136 and the cap 94 is sealed with the container 92 of the vial 48*a* (block 240). The closure arms 115 are then retracted to release the rod 136 so that the arm 132 and the finger 134 may then be rotated, as shown in FIG. 13, to bias the locking tab 96 over the locking strip 100, thereby locking the cap 94 onto the container 92 (block 241).

Though not shown, the capper/decapper assembly 84 may also open the saliva vials 48*c*, or other like vial types, that lack a locking tab 96. Accordingly, the saliva vial 48*c* may be loaded, aligned, and registered with the corresponding spindle 110. The arm 132 and/or the finger 134 of the roller 130 are lowered to rest atop the closed cap 94 of the vial 48*c*. This placement of the arm 132 and/or the finger 134 is/are more appropriate in the instant example because of the relative size of the roller 130 to the saliva vial 48*c*. The spindle 110 also rotates to the rest position and is poised to engage the cap 94.

Because the saliva vial 48*c* lacks the locking tab 96, the first finger 122 will rotate past the saliva vial 48*c* without engaging any portion of the saliva vial 48*c*. With continued rotation, however, the second finger 124 will engage the saliva vial 48*c* to breach, or score, any sealing or tamper evidence tape that may be present on the vial 48*c*. Still further rotation of the spindle 110 causes the cam surface 128 to engage the enlarged tab 97 and bias the cap 94 upwardly. If not already removed, the arm 132 and/or finger 134 are retracted from the cap 94 such that further rotation of the spindle 110 vents the cap 94. The spindle 110 may then return to the rest position.

The cap 94 is opened in a process that is similar to the method described above with respect to the locking-type vial 48*a*. However, the arm 132 and finger 134 of the roller 130 engage the enlarged tab 97 for opening the cap 94. As noted above, great care is taken in properly aligning the components such that neither the finger 134 nor the arm 132 engages any inner surface of the saliva vial 48*c*. Recapping the saliva vial 48*c* may proceed in the manner that was described above with the possibility that the arm 132 and/or finger 134, not the roller 130, engages the cap 94.

Referring one again to FIGS. 1 and 2, with the vials 48*a*, 48*b*, 48*c* recapped and the sample loaded into the vessels 52, the vial and vessel racks 46*a*, 46*b*, 46*c*, 50 may be moved along the transport path 30 from the transfer module 24 to the unload module 28. The vial rack 46*a*, 46*b*, 46*c* is moved by the tooth belt 86 along the barrier wall 82 (or the spacer plate 83, as appropriate). As the vial rack 46*a*, 46*b*, 46*c* extends beyond the toothed belt 86 and into the unload module 28, a second pusher belt 250 engages the toothed surface 57 of the vial rack 46*a*, 46*b*, 46*c* and pulls the vial rack 46*a*, 46*b*, 46*c* onto a second vial conveyer 252. While not specifically shown, the second pusher belt 250 may be enclosed by a wall or housing having a slot through which the pusher 251 extends.

The second vial conveyer 252 includes a belt 254 operably associated with rollers (not shown) and a motor (not shown) that may be controlled by the computer 38. The belt 254 of the second vial conveyer 252 includes one or more pusher walls 256 extending radially outwardly therefrom for abutting and advancing one or more vial racks 46*a*, 46*b*, 46*c* from the transport path 30 to an output end 258. The second vial conveyer 252 is flanked by rails 260 and alignment walls 262. The rails 260 may be an elevated portion of the working surface 44 on which the vial racks 46*a*, 46*b*, 46*c* slide. The alignment walls 262 are spaced by the length of the vial racks 46*a*, 46*b*, 46*c* so as to align the vial rack 46*a*, 46*b*, 46*c* along the second vial conveyer 252. With the vial rack 46*a*, 46*b*, 46*c* conveyed to the output end 258, a user may remove the rack 46*a*, 46*b*, 46*c* from the automated station 20. If not immediately removed, two or more vial racks 46*a*, 46*b*, 46*c* will align at the output end 258 and await removal.

Likewise, the vessel rack 50 may be moved by the first pusher belt 90 along the wall 78. As the vessel rack 50 extends beyond the first pusher belt 90 and into the unload module 28, a third pusher belt 270 engages the end of the vessel rack 50 and pulls the vessel rack 50 along a wall 272 and onto a second vessel conveyer 274. While not specifically shown, the third pusher belt 270 may be enclosed by a wall or housing having a slot through which the pusher 271 extends.

The second vessel conveyer 274 includes a belt 276 operably associated with rollers (not shown) and a motor (not shown) that may be controlled by the computer 38. The belt 276 of the second vessel conveyer 274 includes a plurality of walls 278 radially extending from the belt 276 and spaced to receive a single vessel rack 50 and to advance the vessel racks 50 from the transport path 30 to an output end 280. Like the second vial conveyer 252, the belt 276 of the second vessel conveyer 274 is flanked by alignment walls 282 that are spaced by a length of the vessel rack 50 so as to align the vessel rack 50 along the second vessel conveyer 274. With the vessel rack 50 conveyed to the output end 280, a user may remove the vessel racks 50 from the automated station 20. If not immediately removed, two or more vessel racks 50 will align at the output end 280 and await removal. Again, though not specifically shown, the alignment walls 282 may include one or more optional spacers plates for fitting and conveying vessel racks that are shorter than the examples illustrated herein.

Figure 15:
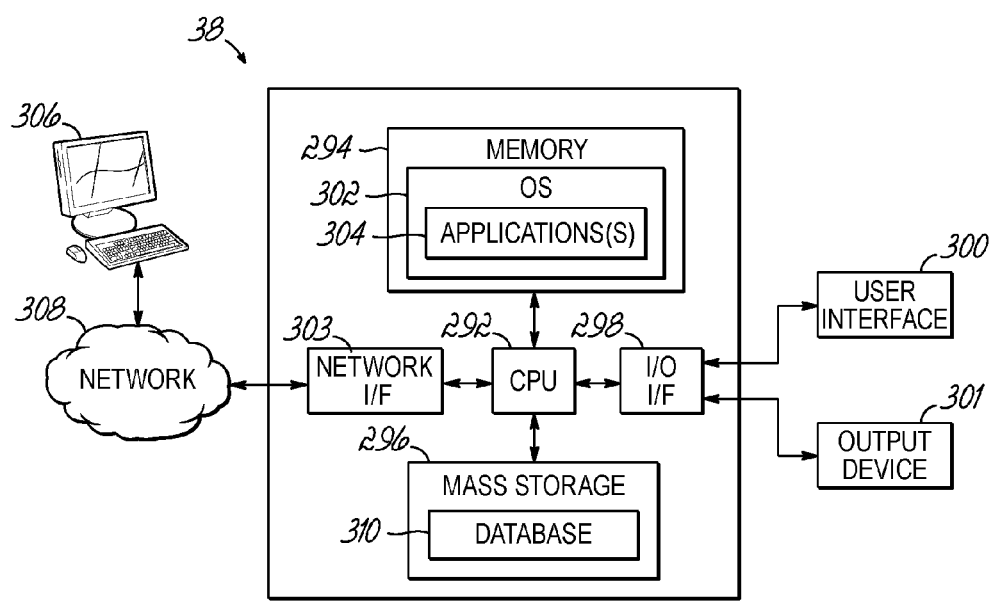
FIG. 15 is a schematic illustration of a computer configured for operating an automated vial capper/decapper station in accordance with embodiments of the present invention.
Figure 16:
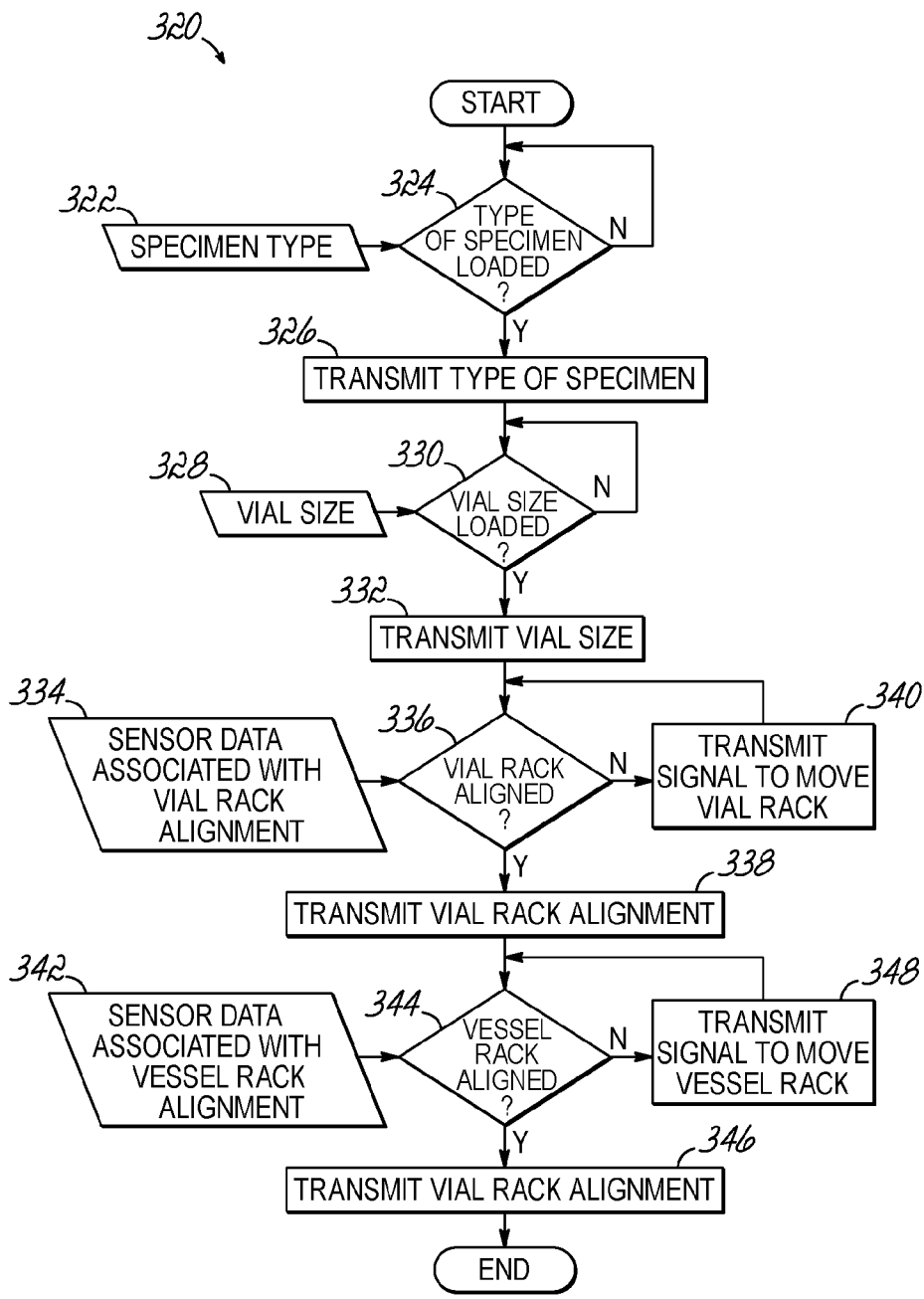
FIG. 16 is a flowchart illustrating a process for loading a vial rack and a vessel rack into a transfer module of an automated vial capper/decapper station in accordance with embodiments of the present invention.
Figure 17:
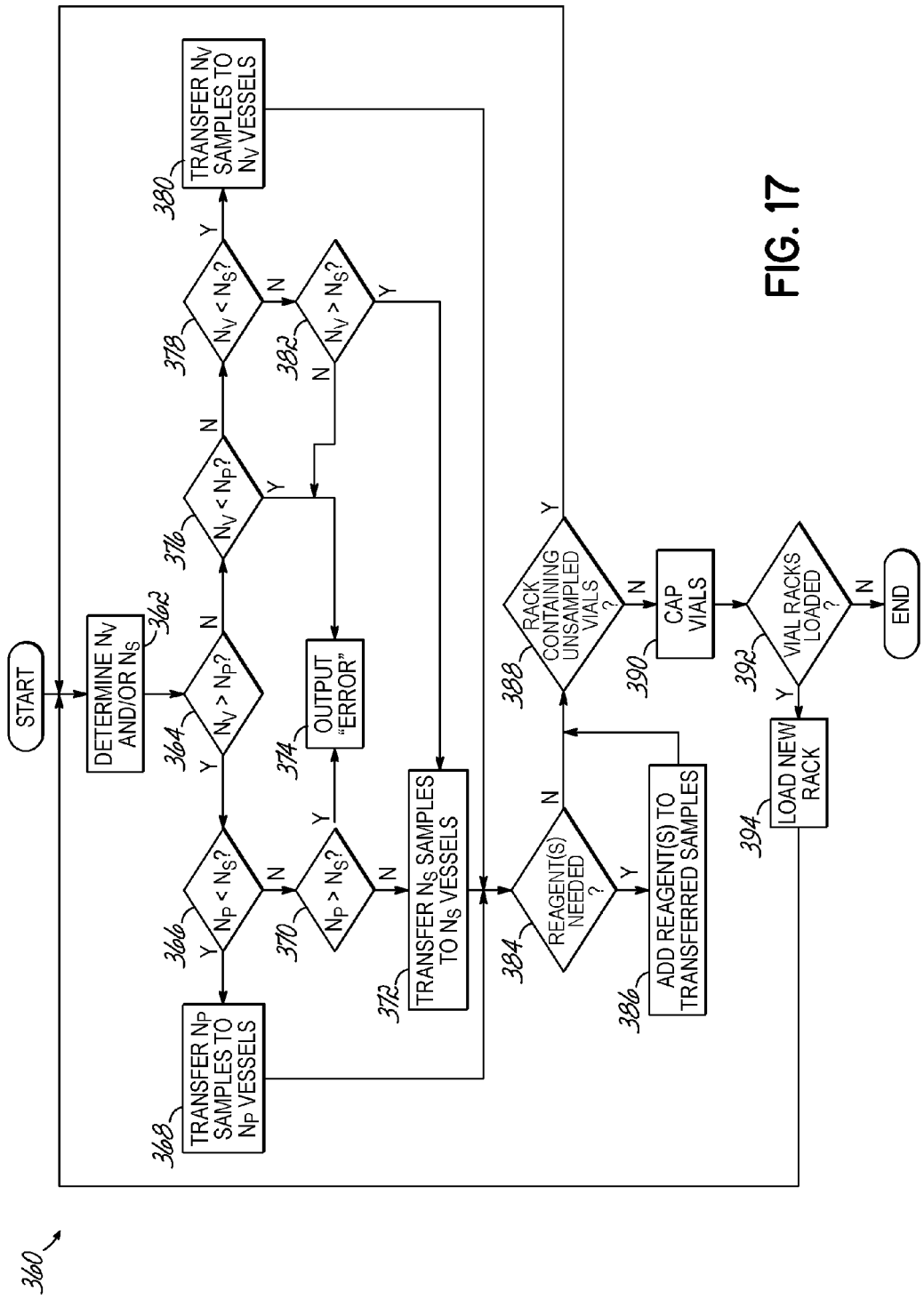
FIG. 17 is a flowchart illustrating a process of transferring a plurality of samples from a plurality of vials to a plurality of vessels in accordance with one embodiment of the present invention.

With the details of the automated station 20 described in detail, and with reference now to FIGS. 15-17, the computer 38 and embodiments of operational logic implemented by the computer 38 for the automated system 20 (FIG. 1) may be described with some detail and in accordance with one embodiment of the present invention.

FIG. 15 illustrates a computer suitable for use with the present invention. The computer 38 that is shown in FIG. 15 may be considered to represent any type of computer, computer system, computing system, server, disk array, or programmable device such as multi-user computers, single-user computers, handheld devices, networked devices, etc. The computer 38 may be implemented with one or more networked computers 306 using one or more networks 308, e.g., in a cluster or other distributed computing system. The computer 38 will be referred to as "computer" for brevity sake, although it should be appreciated that the term "computing system" may also include other suitable programmable electronic devices consistent with embodiments of the invention.

The computer 38 typically includes at least one processing unit (illustrated as "CPU" 292) coupled to a memory 294 along with several different types of peripheral devices, e.g., a mass storage device 296, an input/output interface (illustrated as "I/O I/F" 298) that includes a user interface (including, for example, user input devices and the computer user interface 300) and an output device 301 (such as a printer or other known device), and a network interface 303. The memory 294 may include dynamic random access memory ("DRAM"), static random access memory ("SRAM"), non-volatile random access memory ("NVRAM"), persistent memory, flash memory, at least one hard disk drive, and/or another digital storage medium. The mass storage device 296 typically includes at least one hard disk drive and may be located externally to the computer 38, such as in a separate enclosure or in the one or more networked computers 306, the one or more networked storage devices (not shown but may include, for example, a tape drive), and/or one or more other networked devices (not shown, but may include, for example, a server).

As illustrated in FIG. 15, the computer 38 includes the one CPU 292, which, in various embodiments, may be a single-thread, multi-threaded, multi-core, and/or multi-element processing unit (not shown) as is well known in the art. In alternative embodiments, the computer 38 may include a plurality of CPUs 292 that may include single-thread processing units, multi-threaded processing units, multi-core processing units, multi-element processing units, and/or combinations thereof as is well known in the art. Similarly, the memory 294 may include one or more levels of data, instruction, and/or combination caches, with caches serving the individual processing unit or multiple processing units (not shown) as is well known in the art.

The memory 294 of the computer 38 may include an operating system (illustrated as "OS" 302) to control the primary operation of the computer 38 in a manner that is well known in the art. The memory 294 may also include at least one application 304, or other software program, configured to execute in combination with the operating system 302 and perform a task, such as sample preparation and/or indexing and tracking of biological fluid specimens as described herein. The mass storage device 296 may further include one or more databases 310 having data corresponding to the biological fluid specimen loaded into the automated station 20 (FIG. 1), details as to the standards 230 (FIG. 2) and dilutions of the respective assays or sample preparations, and so forth.

In general, the routines executed to implement the embodiments of the present invention, whether implemented as part of the operating system 302 or a specific application 304, component, algorithm, program, object, module or sequence of instructions, or even a subset thereof, will be referred to herein as "computer program code" or simply "program code." Program code typically comprises one or more instructions that are resident at various times in the memory 294 and/or the mass storage devices 296 in the computer 38, and that, when read and executed by the processing unit 292 in the computer 38, causes the computer 38 to perform the processes necessary to or elements embodying the various aspects of the present invention.

Those skilled in the art will recognize that the environment illustrated in FIG. 15 is not intended to limit the present invention. Indeed, those skilled in the art will recognize that other alternative hardware and/or software environments may be used without departing from the scope of the present invention.

Turning now to FIG. 16, with reference also to FIGS. 1 and 2, a flowchart 320 illustrating a process flow by which the computer 38 (FIG. 15) may be used to index the vial racks 46a, 46b, 46c through the automated station 20 for transferring one or more samples accordingly is shown and described in accordance with one embodiment of the present invention. The types of biological fluid specimens that are being loaded into the automated system 20 are determined (block 324) from biological fluid specimen type information input by the user or loaded from a centralized database (block 322). The biological fluid specimen type may alternatively be associated with information corresponding to a barcode or RFID antenna that is included on the vial 48a, 48b, 48c. When the type of biological fluid specimen information is received ("Yes" branch of decision block 324), then the computer 38 (FIG. 15) will transmit the type of biological fluid specimen to the fluid handling system 26 (block 326). If data related to the type of biological fluid specimen is not received ("No" branch of decision block 324), then the process restarts.

Because the automated station 20 as illustrated and discussed previously may be configured to handle one or more vial sizes, data related to the vial size (block 328) within the loaded rack 46a, 46b, 46c entering the transport path 30 is determined (block 330). If the vial size data is received ("Yes" branch of decision block 330), then the process continues by transmitting the vial size to the fluid handling system 26 (block 332). If the vial size data is not loaded ("No" branch of decision block 330), then the process may return and further awaits the vial size data.

Before a sample of the biological fluid specimen may be transferred from the vial 48a, 48b, 48c to the vessel 52, the vial and vessel racks 46a, 46b, 46c, 50 must be properly aligned within the capper/decapper assembly 84. Accordingly, a sensor (not shown) associated with the transport path 30 may acquire and transmit data that is associated with the vial rack position (block 334). If the vial rack 46a, 46b, 46c is aligned according to a previously determined setting (for example, the edge of the rack 46a, 46b, 46c being positioned at the sensor) ("Yes" branch of decision block 336), then the vial rack 46a, 46b, 46c is aligned and the process may continue by transmitting an indication of alignment (block 338). If the vial rack 46a, 46b, 46c is not so aligned ("No" branch of decision block 336), then a signal may be sent or transmitted to the toothed belt 86 to reposition the vial rack 46a, 46b, 46c (block 340) and the inquiry regarding vial rack position is made again (block 336).

After the vial rack 46a, 46b, 46c is properly positioned, a similar inquiry is made regarding the vessel rack 50. Accordingly, a sensor (not shown) associated with the transport path 30 may acquire and transmit data that is associated with the position of the vessel rack 50 (block 342). If the vessel rack 50 is aligned according to a previously determined setting (for example, the edge of the vessel rack 50 being positioned at the sensor) ("Yes" branch of decision block 344), then the vessel rack 50 is aligned with transmission of an indication of such (block 346) and the process may end. If the vessel rack 50 is not so aligned ("No" branch of decision block 344), then a signal may be sent or transmitted to the first pusher belt 90 to reposition the vessel rack 50 (block 348) and the inquiry regarding vessel rack position is made again (block 344).

Because the automated system 20 may be configured to accommodate vials of varying sizes and one or more styles of racks containing varying numbers of vials, the automated system 20 may include a method of indexing and tracking the number of vials entering the capper/decapper assembly 84 and the most efficient manner of transferring biological fluid specimens from the vials 48a, 48b, 48c to the vessels 52.

FIG. 17 is a flowchart 360 illustrating one method of indexing and tracking samples in the automated system 20 according to one embodiment of the present invention and is described below with reference to FIGS. 1 and 2. After the racks 46a, 46b, 46c, 50 are properly loaded and aligned, for example, by the method that was described in the flowchart 320 (FIG. 16), the vial size contained within the vial rack 46a, 46b, 46c (vial size data from block 328 of FIG. 16) may be used to determine a number of vials loaded ("$N_v$") while the number of vessels 52 available to receive a sample is determined ("$N_s$") (block 362). For example, if all openings within the 90 mL vial rack 46b are filled with 90 mL vials 48b, then $N_v=5$; if all openings within the 45 mL vial rack 46a are filled with 45 mL vials 48a, then $N_v=10$; if the openings within the saliva vial rack 46c are filled with saliva vials 48c as shown in FIG. 2, then $N_v=8$. However, not all openings within the vial rack 46a, 46b, 46c need necessarily be filled.

As was described above, the fluid handling system 26 may include a pipetter having a number of channels. The number of channels ("$N_p$") determines the maximum number of samples that may be transferred simultaneously from the vials 48a, 48b, 48c to the vessels 52. For example, and for illustrative purposes herein only, $N_p=8$.

As with the instant example, and may often be the circumstance, $N_p$ does not equal $N_v$ or $N_s$ (for illustrative purposes here, the $N_s=10$). Therefore, for the most efficient transfer of samples, $N_p$ is compared with $N_v$. If $N_p$ is greater than $N_v$ ("Yes" branch of decision block 364), then an inquiry is made as to whether $N_p$ is less than $N_s$ (block 366). If the number of channels is less than the number of vessels available to receive samples ("Yes" branch of decision block 366), then $N_p$ samples are transferred to $N_p$ vessels (block 368). If $N_p$ was greater than $N_s$ ("No" branch of decision block 366 and "Yes" branch of decision block 370), then only $N_s$ samples may be transferred to $N_s$ vessels (block 372). If the $N_p>N_s$ decision cannot be answered affirmatively ("No" branch of decision block 370), then "Error" is output (block 374).

Returning again to the $N_v>N_p$ decision (block 364), if the number of vials was less than the number of pipetting channels ("No" branch of decision block 364 and "Yes" branch of decision block 376), then an inquiry is made as to whether $N_v$ is less than $N_s$ (block 378). If the number of vials is less than the number of vessels available to receive samples ("Yes" branch of decision block 378), then $N_v$ samples are transferred to $N_v$ vessels (block 380). If $N_v$ was greater than $N_s$ ("No" branch of decision block 378 and "Yes" branch of decision block 382), then only $N_s$ samples may be transferred to $N_s$ vessels (block 372). If the $N_v>N_s$ decision cannot be answered affirmatively ("No" branch of decision block 382), then "Error" is output (block 374).

As was noted briefly above, the preparation of biological fluid specimens may be partially dependent on the type of biological fluid specimen to be analyzed and may require the addition of one or more standards 230 to the vessel 52. If standards 230 (illustrated and described in FIG. 17 as "REAGENTS") are needed ("Yes" branch of decision block 384), then one or more reagents may be aspirated by the pipetter and dispensed into the respective vessel 52 containing the transferred sample (block 386). If no reagent is necessary or desired ("No" branch of decision block 384), then the process continues. It will be understood that while the addition of reagents to the vessels 52 is illustrated in FIG. 17 as being after the sample transfer, the addition of reagents could instead precede sample transfer.

While not specifically shown herein, the types of reagents that are added to the vessel 52 need not be constant for all vessels 52 within a rack 50. For example, a given rack 50 may include two or more different biological fluid specimen types to be analyzed. Accordingly, the fluid handling system 26 may use the biological fluid specimen type data (block 322 of FIG. 16) to determine an identity of the particular biological fluid specimen associated with a select one vial 48a, 48b, 48c and then add reagents to the appropriate vessel 52 in accordance with a previously determined assay. Furthermore, it would be understood that all vials 48a, 48b, 48c within a particular vial rack 46a, 46b, 46c may contain the same biological fluid specimen type and thus be treated in accordance with the same previously determined assay or the vials 48a, 48b, 48c may contain different biological fluid specimen types, and individual processing may be required.

After the sampling and the addition of reagents, as necessary, is complete, it may be determined whether the rack 46a, 46b, 46c loaded into the capper/decapper assembly 84 still contains unsampled vials 48a, 48b, 48c (block 388). If there are unsampled vials 48a, 48b, 48c within the loaded rack 46a, 46b, 46c ("Yes" branch of decision block 388), then the process returns to determine a new $N_v$ (block 362). However, if all vials 48a, 48b, 48c within the loaded rack 46a, 46b, 46c have been sampled ("No" branch of decision block 388), then the capper/decapper assembly 84 may be activated to recap the vials 48a, 48b, 48c within the rack (block 390) and there is an inquiry as to whether additional racks 46a, 46b, 46c have been loaded into the load module 22 and await sampling (block 392). If more racks 46a, 46b, 46c are positioned within the load module 22 ("Yes" branch of decision block 392), then the loaded rack 46a, 46b, 46c is transferred along the transport path 30, out of the capper/decapper assembly 84, a new rack 46a, 46b, 46c is loaded into the capper/decapper assembly 84 (block 394), and the process continues (return to block 362). If no other racks 46a, 46b, 46c are within the load module 22 ("No" branch of decision block 392), then the loaded rack 26 is transferred along the transport path 30 from the capper/decapper assembly 84 and the process ends.

Figure 18:
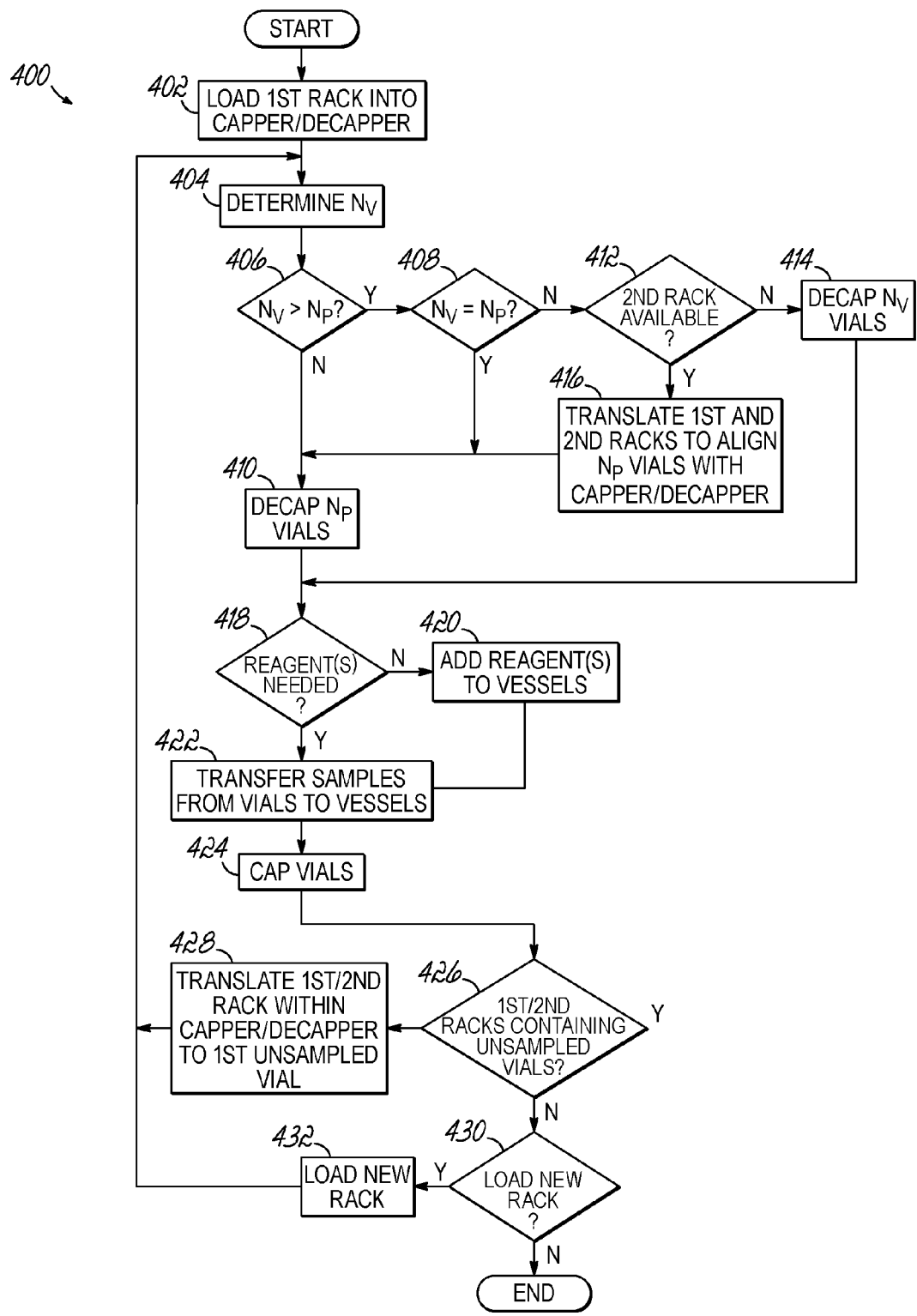
FIG. 18 is a flowchart illustrating another process of transferring a plurality of samples from a plurality of vials to a plurality of vessels in accordance with another embodiment of the invention.

In an alternative method of using the automated system 20, the number of unsampled vials $N_v$ opened by the capper/decapper assembly 84 is set to maximize the use of the fluid handling system 26. For example, a flowchart 400 is shown in FIG. 18 that illustrates another method of indexing and tracking the samples in the automated system 20 and is described in accordance with another embodiment of the present invention and with reference also to FIGS. 1 and 2. It will be appreciated that in the particular illustrated process, $N_v$ will equal $N_s$. A first vial rack 46a, 46b, 46c is loaded into the capper/decapper assembly 84 (block 402) such that $N_v$ may be determined (block 404) and compared with $N_p$ (block 406). If $N_v$ is greater than $N_p$ ("Yes" branch of block 406), or $N_v$ is equal to $N_p$ ("Yes" branch of block 408), then $N_p$ vials are decapped (block 410). However, if $N_v$ is less than $N_p$ ("No" branch of block 406 and block 408), then an inquiry is made was to whether a second rack 46a, 46b, 46c is available within the load module 22 (block 412). If there are no other racks 46a, 46b, 46c in the load module 22 ("No" branch of block 412), then $N_v$ vials are decapped (block 414). If a second rack 46a, 46b, 46c is within the load module 22 ("Yes" branch of block 412), then the toothed belt 86 will translate the first vial rack 46*a*, 46*b*, 46*c* within the capper/decapper assembly 84 so that the first unsampled vial 48*a*, 48*b*, 48*c* of the first vial rack 46*a*, 46*b*, 46*c* aligns with the first spindle 110 of the capper/decapper assembly 84. The push bar 80 and the toothed belt 86 will translate the second vial rack 46*a*, 46*b*, 46*c* into the capper/decapper assembly 84 until $N_p$ vials are positioned within the capper/decapper assembly 84 and aligned with the spindles 110 (block 416). It will be readily appreciated that the vial racks 46*a*, 46*b*, 46*c* may be designed such that the distance between a vial at the ends of the plurality of vials 48*a*, 48*b*, 48*c* and the lateral end of the vial racks 46*a*, 46*b*, 46*c* is about ½ the distance between successive vials 48*a*, 48*b*, 48*c* within the vial rack 46*a*, 46*b*, 46*c*. In this way, two vial racks 46*a*, 46*b*, 46*c* may be adjacently positioned and the distance between successive vials remains constant within a vial rack and between vial racks. After the first and second vial racks 46*a*, 46*b*, 46*c* are aligned, $N_p$ vials are decapped (block 410).

With the optimal number of vials 48*a*, 48*b*, 48*c* decapped, an inquiry is made as to whether standards 230 (illustrated and described in FIG. 18 as "REAGENTS") are needed (block 418). If reagents are needed for the particular selected assay ("Yes" branch of decision block 418), then one or more reagents may be aspirated and dispensed into the respective vessel 52 (block 420). Otherwise ("No" branch of decision block 418), the process continues.

With the vials 48*a*, 48*b*, 48*c* decapped, the fluid handling system 26 may transfer the optimal number of samples in a manner that was described above in some detail (block 422). The capper/decapper assembly 84 is then activated to cap the vials 48*a*, 48*b*, 48*c* as was also described previously (block 424).

After the vials 48*a*, 48*b*, 48*c* are capped, an inquiry is made as to whether any loaded vial rack 46*a*, 46*b*, 46*c* contains unsampled vials 48*a*, 48*b*, 48*c* (block 426). For example, if only the first vial rack 46*a*, 46*b*, 46*c* is loaded, then the determination inquires as to whether any further unsampled vials 48*a*, 48*b*, 48*c* remain in the first vial rack 46*a*, 46*b*, 46*c*. If first and second vial racks 46*a*, 46*b*, 46*c* are loaded, then the first vial rack 46*a*, 46*b*, 46*c* is removed and the determination inquires as to whether any further unsampled vials 48*a*, 48*b*, 48*c* remain in the second vial rack 46*a*, 46*b*, 46*c*. If unsampled vials exist ("Yes" branch of decision block 426), then the first or second vial rack 46*a*, 46*b*, 46*c*, as appropriate, is translated along the transport path 30 such that the first unsampled vial 48*a*, 48*b*, 48*c* aligns with the first spindle 110 of the capper/decapper assembly 84 (block 428). Otherwise ("No" branch of decision block 426), the loaded vial rack(s) 46*a*, 46*b*, 46*c* is/are transferred out of the capper/decapper assembly 84 and the automated system 20 determines whether another vial rack 46*a*, 46*b*, 46*c* resides within the load module 22 (block 430). If another vial rack 46*a*, 46*b*, 46*c* resides within the load module 22 ("Yes" branch of decision block 430), then a new vial rack 46*a*, 46*b*, 46*c* is loaded into the capper/decapper assembly 84 (block 432) and the process continues (return to block 404). Otherwise ("No" branch of decision block 430), the process ends.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A liquid transfer system having a transport path configured to transport a plurality of vials through the liquid transfer system, each of the plurality of vials having an open-ended vial body and a cap connected to the vial body and forming a seal therewith, comprising:
 a vial capper/decapper assembly positioned adjacent the transport path and comprising:
  a plurality of rotatable spindles, each of the plurality of rotatable spindles having a rotatable shaft and a first projection supported by the shaft and having a cam surface configured to engage a respective cap so as to breach the seal formed by the cap with the vial body and open the cap relative to the vial body upon rotation of the respective one of the plurality of rotatable spindles,
 wherein the plurality of rotatable spindles is configured to rotate simultaneously so as to simultaneously breach the seals and open the caps of the plurality of vials.

2. The liquid transfer system of claim 1, wherein each of the plurality of vials includes a tab locking the cap closed with the vial body in a first position of the tab and unlocking the cap with the vial body in a second position of the tab, the vial capper/decapper assembly further comprising:
 a second projection supported by the shaft configured to engage a tab of the respective vial so as to move the tab from the first position to the second position upon rotation of the respective one of the plurality of rotatable spindles.

3. The liquid transfer system of claim 2, wherein the second projection is axially offset from the first projection.

4. The liquid transfer system of claim 2, wherein the first projection is located axially above the second projection.

5. The liquid transfer system of claim 2, wherein the second projection expands circumferentially.

6. The liquid transfer system of claim 1, wherein the first projection expands circumferentially.

7. The liquid transfer system of claim 1, wherein the cam surface of the first projection is inclined about the shaft.

8. The liquid transfer system of claim 1, further comprising:
 a rotating arm assembly configured to engage the opened caps and to retract the opened caps away from the vial body.

9. The liquid transfer system of claim 8, wherein the rotating arm assembly includes a plurality of rollers spaced apart and registered with one of the plurality of rotatable spindles.

10. The liquid transfer system of claim 9, wherein the plurality of rollers is coupled to a rotatable rod defining a first rotatable axis about which the rotating arm assembly is configured to rotate to engage the opened caps.

11. The liquid transfer system of claim 10, wherein the rotatable rod is coupled to at least one support configured to rotate about a second rotatable axis.

12. The liquid transfer system of claim 9, wherein each of the plurality of rollers includes an arm extending radially therefrom and configured to engage the opened cap.

13. The liquid transfer system of claim 12, wherein the arm further includes a finger that extends angularly away from a distal end of the arm, the finger configured to extend around an edge of the opened cap when the arm engages the opened cap.

14. The liquid transfer system of claim 1, wherein the plurality of vials is supported within a vial rack and the transport path is configured to move the vial rack through the liquid transfer system.

15. The liquid transfer system of claim 14, wherein the transport path further comprises:
   a spacer plate positionable within the transport path such that the transport path is configured to move a vial rack of a first size through the liquid transfer system when the spacer plate is positioned within the transport path and is further configured to transfer a vial rack of a second size through the liquid transfer system when the spacer plate is not positioned within the transport path.

16. A liquid transfer system having a transport path configured to transport at least one vial through the liquid transfer system, the vial having an open-ended vial body and a cap connected to the vial body and forming a seal therewith, comprising:
   a vial capper/decapper assembly comprising:
      at least one spindle positioned adjacent the transport path and having a rotatable shaft, a first projection supported by the shaft, and a cam surface configured to engage a respective cap so as to breach the seal formed by the cap with the vial body and open the cap relative to the vial body upon rotation of the at least one spindle; and
      a rotating arm assembly positioned adjacent the transport path and opposite the at least one spindle, the rotating arm assembly configured to engage the opened caps and to retract the opened caps away from the vial body.

17. The liquid transfer system of claim 16, wherein the at least one vial includes a tab locking the cap with the vial body in a first position of the tab and unlocking the cap with the vial body in a second position of the tab, the vial capper/decapper assembly further comprising:
   a second projection supported by the shaft and being configured to engage the tab of the at least one vial so as to move the tab from the first position to the second position upon rotation of the spindle.

18. The liquid transfer system of claim 17, wherein the second projection is axially offset from the first projection.

19. The liquid transfer system of claim 17, wherein the first projection is located axially above the second projection.

20. The liquid transfer system of claim 17, wherein the second projection expands circumferentially.

21. The liquid transfer system of claim 16, wherein the first projection expands circumferentially.

22. The liquid transfer system of claim 16, wherein the cam surface of the first projection is inclined about the shaft.

23. The liquid transfer system of claim 16, wherein the rotating arm assembly is aligned with the at least one spindle across the transport path.

24. The liquid transfer system of claim 16, wherein the rotating arm assembly is operably coupled to a rotatable rod defining a first rotatable axis.

25. The liquid transfer system of claim 24, wherein the rotatable rod is operably coupled to at least one support that is configured to rotate about a second rotatable axis.

26. The liquid transfer system of claim 16, wherein the rotating arm assembly includes an arm extending radially therefrom and is configured to engage the opened cap.

27. The liquid transfer system of claim 26, wherein the arm further includes a finger that extends angularly away from a distal end of the arm, the finger configured to extend around an edge of the opened cap when the arm engages the opened cap.

28. An automated liquid sample transfer system having a transport path configured to transport a plurality of vials through the automated liquid transfer system, each of the plurality of vials having an open-ended vial body containing a biological fluid and a cap connected to the vial body and forming a seal therewith, the automated liquid sample transfer system comprising:
   a load module;
   an unload module;
   a transfer module positioned between the load and unload modules; and
   a vial capper/decapper assembly positioned adjacent the transport path and comprising:
      a plurality of rotatable spindles, each of the plurality of rotatable spindles having a rotatable shaft and a first projection supported by the shaft and having a cam surface configured to engage the cap of a respective one of the plurality of vials so as to breach the seal formed by the cap with the vial body and open the cap relative to the vial body upon rotation of the respective one of the plurality of rotatable spindles, wherein the plurality of rotatable spindles is configured to rotate simultaneously so as to simultaneously breach the seals and open the caps of the plurality of vials.

29. The automated liquid transfer system of claim 28, wherein each of the plurality of vials includes a tab locking the cap closed with the vial body in a first position of the tab and unlocking the cap with the vial body in a second position of the tab, the vial capper/decapper assembly further comprising:
   a second projection supported by the shaft and being configured to engage a tab of a respective vial so as to move the tab from the first position to the second position upon rotation of the respective one of the plurality of rotatable spindles.

30. The automated liquid transfer system of claim 28, further comprising:
   a rotating arm assembly positioned adjacent the transport path and opposite the plurality of rotatable spindles and configured to engage the opened caps and to retract opened caps away from the vial body, wherein the rotating arm assembly includes a plurality of rollers that corresponds to the plurality of rotatable spindles.

31. The automated liquid sample transfer system of claim 28, wherein the automated liquid sample transfer system is further configured to transport a plurality of vessels through the automated liquid transfer system, each of the plurality of vessels has an open-ended vessel body.

32. The automated liquid sample transfer system of claim 31, wherein the plurality of vials is supported within a vial rack and the plurality of vessels is support within a vessel rack, the transport path having a vial rack path and a vessel rack path configured to transport the vial rack and the vessel rack, respectively, through the liquid transfer system.

33. The automated liquid transfer system of claim 32, further comprising:
   a rotating arm assembly positioned adjacent the transport path and opposite the plurality of rotatable spindles and configured to engage the opened caps and to retract the opened caps away from the vial body, wherein each of the rotating arm assembly includes a plurality of rollers that corresponds to the plurality of rotatable spindles.

34. The automated liquid transfer system of claim 33, further comprising:
   a plurality of pipette tips positioned along the transport path between the plurality of rotatable spindles and the plurality of rollers, the plurality of pipette tips configured to transfer an aliquot of the biological fluid from one or more of the plurality of vials to one or more of the plurality of vessels.

35. A method of capping/decapping a plurality of vials, each of the plurality of vials having an open-ended vial body and a cap connected to the vial body and forming a seal therewith, the method comprising:
   aligning the plurality of vials with a plurality of rotatable spindles, each of the plurality of rotatable spindles having a rotatable shaft, a first projection supported by the shaft, and a cam surface;
   simultaneously rotating the plurality of rotatable spindles such that the first projection of each of the plurality of rotatable spindles breaches the seals; and
   continuing the simultaneous rotation such that the cam surface of each of the plurality of rotatable spindles opens the caps of the plurality of vials.

36. The method of claim 35, wherein each of the plurality of vials includes a tab locking the cap with the vial body in a first position of the tab and unlocking the cap with the vial body in a second position of the tab, the method further comprising:
   simultaneously rotating the plurality of rotatable spindles such that a second projection supported by the shaft engages a tab of a respective vial and moves the tab from the first position to the second position.

37. The method of claim 35, wherein the plurality of vials is aligned with and spaced away from a rotating arm assembly, the method further comprising:
   advancing the rotating arm assembly toward opened caps of the plurality of vials;
   engaging each of the opened caps with the rotating arm assembly; and
   retracting the opened caps with the rotating arm assembly away from the vial body.

38. The method of claim 37, wherein the rotating arm assembly includes a plurality of rollers, each having a radially extending arm that engages each opened cap.

39. The method of claim 37, further comprising:
   advancing the rotating arm assembly to advance the caps onto each open-ended vial body of each of the plurality of vials; and
   continuing the advancing to seal the caps with the vial body.

40. The method of claim 39, wherein the rotating arm assembly includes a plurality of rollers, each having a radially extending arm, and each of the plurality of vials includes a tab locking the cap with the vial body in a first position of the tab and unlocking the cap with the vial body in a second position of the tab, the method further comprising:
   rotating the plurality of rollers such that the arms move the tab from the second position to the first position.

* * * * *

UNITED STATES PATENT AND TRADEMARK OFFICE
CERTIFICATE OF CORRECTION

| | | |
|---|---|---|
| PATENT NO. | : 9,052,299 B2 | Page 1 of 1 |
| APPLICATION NO. | : 13/358058 | |
| DATED | : June 9, 2015 | |
| INVENTOR(S) | : Lloyd A. Jones et al. | |

It is certified that error appears in the above-identified patent and that said Letters Patent is hereby corrected as shown below:

In the Specification:
In column 1, line 13, change "to a system and method for automatic opening and closing the lid" to --to a system and method for automatically opening and closing the lid--.

In column 2, line 49, change "such that the first projection of each of spindle breaches" to --such that the first projection of each spindle breaches--.

In column 6, line 25, change "such that as the push bar 80 translates" to --such that the push bar 80 translates--.

In column 10, line 62, change "for periodic rinsing the fluid handling system 26" to --for periodically rinsing the fluid handling system 26--.

In column 12, line 56, change "one or more optional spacers plates" to --one or more optional spacer plates--.

In column 15, line 36, change "If Np is greater than Np" to --If Nv is greater than Np--.

In the Claims:
In claim 32, column 20, line 51, change "the plurality of vessels is support within a vessel" to --the plurality of vessels is supported within a vessel--.

In claim 33, column 20, line 61, change "wherein each of the rotating arm assembly includes" to --wherein each of the rotating arm assemblies includes--.

Signed and Sealed this
Twenty-fourth Day of November, 2015

Michelle K. Lee
*Director of the United States Patent and Trademark Office*